US011142585B2

(12) United States Patent
Tan et al.

(10) Patent No.: US 11,142,585 B2
(45) Date of Patent: Oct. 12, 2021

(54) ANTI-ERBB-2 ANTIBODIES AND USES THEREOF

(71) Applicant: Agency for Science, Technology and Research, Singapore (SG)

(72) Inventors: Heng Liang Tan, Singapore (SG); Andre Boon Hwa Choo, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 230 days.

(21) Appl. No.: 16/301,382

(22) PCT Filed: May 12, 2017

(86) PCT No.: PCT/SG2017/050253
§ 371 (c)(1),
(2) Date: Nov. 13, 2018

(87) PCT Pub. No.: WO2017/196263
PCT Pub. Date: Nov. 16, 2017

(65) Prior Publication Data

US 2020/0325246 A1 Oct. 15, 2020

(30) Foreign Application Priority Data

May 12, 2016 (SG) .......................... 10201603812X

(51) Int. Cl.
*C07K 16/40* (2006.01)
*A61K 47/68* (2017.01)
*A61K 39/395* (2006.01)
*A61K 51/10* (2006.01)

(52) U.S. Cl.
CPC .......... *C07K 16/40* (2013.01); *A61K 39/3955* (2013.01); *A61K 47/6803* (2017.08); *A61K 51/1075* (2013.01); *C07K 2317/565* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 7,371,376 | B1 | 5/2008 | Fendly |
| 2002/0001587 | A1 | 1/2002 | Erickson et al. |
| 2009/0311262 | A1 | 12/2009 | Arribas Lopez et al. |
| 2015/0366987 | A1 | 12/2015 | Bodyak et al. |

FOREIGN PATENT DOCUMENTS

| | | | |
|---|---|---|---|
| EP | 2998319 | B1 | 5/2014 |
| EP | 2998319 | A1 | 3/2016 |
| WO | 2001/09187 | A2 | 2/2001 |
| WO | 0109187 | A3 | 2/2001 |
| WO | 2007/147165 | A2 | 12/2007 |
| WO | 2007147165 | A3 | 12/2007 |
| WO | 2011/147986 | A1 | 12/2011 |
| WO | 2011147986 | A1 | 12/2011 |
| WO | 2017167967 | A1 | 10/2017 |

OTHER PUBLICATIONS

Lederman et al (Molecular Immunology 28:1171-1181, 1991) (Year: 1991).*

Li et al (Proc. Natl. Acad. Sci. USA 77:3211-3214, 1980) (Year: 1980).*

Paul, p. 293, first column, lines 3-8 and line 31 to col. 2, line 9 and lines 27-30, 1993 (Year: 1993).*

Rudikoff et al (Proc. Natl. Acad. Sci. USA, 79(6):1979-1983, Mar. 1982) (Year: 1982).*

Colman P. M. (Research in Immunology, 145:33-36, 1994) (Year: 1994).*

The extended European Search Report for European Application No. 17796503.5 dated Dec. 4, 2019, 8 pages.

The International Preliminary Report on Patentability for PCT Application No. PCT/SG2017/050253 dated Nov. 13, 2018, 8 pages.

Klapper et al., "A subclass of tumor-inhibitory monoclonal antibodies to ErbB-2/HER2 blocks crosstalk with growth factor receptors," Oncogene, 14: 2099-2109, 1997.

Uniprot Accession No. P04626-4, Oct. 2007, [Retrieved on Jan. 9, 2019 from http://www.uniprot.org/uniprot/P04626].

Ward et al., "Truncated p110 ERBB2 induces mammary epithelial cell migration, invasion and orthotopic xenograft formation, and is associated with loss of phosphorylated STAT5," Oncogene, 32: 2463-2474, 2013.

Matsuzaki et al., "Potential targets for ovarian clear cell carcinoma: a review of updates and future perspectives," Cancer Cell. Int., 15:117, 13 pages, 2015.

Serafino, "Roche Drug Combination Shows No Added Benefit in Study," Bloomberg L.P. [Retrieved from https://www.bloomberg.com/news/articles/2014-12-19/roche-drug-combination-shows-no-added-benefit-in-study], Dec. 19, 2014.

(Continued)

*Primary Examiner* — Padmavathi Baskar

(74) *Attorney, Agent, or Firm* — Womble Bond Dickinson (US) LLP

(57) ABSTRACT

The present invention relates to antigen-binding proteins, or antigen-binding fragments thereof. In particular, the present invention relates to antigen-binding proteins, or antigen-binding fragments thereof that bind to ERBB2. Compositions comprising a physiologically acceptable carrier and a therapeutically effective amount of the antigen-binding protein, or antigen-binding fragment thereof, use of the antigen-binding protein, or antigen-binding fragment thereof, methods for detecting cancer as well as kits when used in such methods are also provided.

12 Claims, 22 Drawing Sheets

Specification includes a Sequence Listing.

(56) References Cited

OTHER PUBLICATIONS

Helwick, "Ado-Trastuzumab Emtansine Fails to Replace Standard of Care in First-Line Metastatic Breast Cancer," The ASCO Post [Retrieved on Jan. 14, 2019 from http://www.ascopost.com/issues/july-10-2015/ado-trastuzumab-emtansine-fails-to-replace-standard-of-care-in-first-line-metastatic-breast-cancer/], 6 pages, Jul. 10, 2015.
Wasserman, "Roche's bid to sub Kadcyla for Herceptin takes a big hit with lackluster PhIII data," FiercePharma [Retrieved on Jan. 14, 2019 from https://www.fiercepharma.com/regulatory/roche-s-bid-to-sub-kadcyla-for-herceptin-takes-a-big-hit-lackluster-phiii-data], 4 pages, Dec. 19, 2014.
Garde, "Roche's Kadcyla flunks a gastric cancer study," FiercePharma [Retrieved on Jan. 14, 2019 from https://www.fiercebiotech.com/r-d/roche-s-kadcyla-flunks-a-gastric-cancer-study], 4 pages, Oct. 22, 2015.
Wasserman, "U.K. cost watchdog gives one-two punch to Roche's Kadcyla and BMS' Opdivo," FiercePharma [Retrieved on Jan. 14, 2019 from https://www.fiercepharma.com/financials/u-k-cost-watchdog-gives-one-two-punch-to-roche-s-kadcyla-and-bms-opdivo], 4 pages, Dec. 16, 2015.
Holliger et al., "Engineered antibody fragments and the rise of single domains," Nature Biotechnology, 23(9): 1126-1136, Sep. 2005.
Richman et al., "HER2 overexpression and amplification as a potential therapeutic target in colorectal cancer: analysis of 3256 patients enrolled in the QUASAR, FOCUS and PICCOLO colorectal cancer trials," J. Pathol., 238: 562-570, Jan. 26, 2016.
Wasserman, "Kadcyla's miss in stomach cancer dents Roche's effort to reap more from new drugs," FiercePharma [Retrieved on Jan. 10, 2019 from https://www.fiercepharma.com/regulatory/kadcyla-s-miss-stomach-cancer-dents-roche-s-effort-to-reap-more-from-new-drugs], 3 pages, Oct. 23, 2015.
Kan et al., "Up-regulation of HER2 by gemcitabine enhances the antitumor effect of combined gemcitabine and trastuzumab emtansine treatment on pancreatic ductal adenocarcinoma cells," BMC Cancer, 15:726, 9 pages, 2015.
Oh et al., "HER2 as a novel therapeutic target for cervical cancer," Oncotarget, 6(34): 36219-36230, Sep. 21, 2015.
Wasserman, "Roche provides update on Phase III MARIANNE study in people with previously untreated advanced HER2-positive breast cancer," FiercePharma [Retrieved on Jan. 10, 2019 from https://www.fiercepharma.com/pharma/roche-provides-update-on-phase-iii-marianne-study-people-previously-untreated-advanced-her2], 4 pages, Dec. 19, 2014.
Mazieres et al., "Lung cancer patients with HER2 mutations treated with chemotherapy and HER2-targeted drugs: results from the European EUHER2 cohort," Annals of Oncology, 27: 281-286, Nov. 23, 2015.
Siegel et al., "HER2/ERBB2 immunoreactivity in human retinoblastoma," Tumour Biol., 37(5): 6135-6142, May 2016.
International Search Report and the Written Opinion of the International Searching Authority for International Application No. PCT/SG2017/050253 dated Jul. 3, 2017.
The Written Opinion for Singaporean Application No. 11201810032P dated Mar. 23, 2020, 8 pages.
The Written Opinion of Singaporean Application No. 11201810032P dated Apr. 8, 2021, 11 pages.
Klapper et al., "A subclass of tumor-inhibitory monoclonal antibodies to ErbB-2/HER2 blocks crosstalk with growth factor receptors", Nature, Jan. 10, 1997, 11 pages.
Ward et al., "Truncated p110 ERBB2 induces mammary epithelial cell migration, invasion and orthotopic xenograft formation, and is associated with loss of phosphorylated STAT5", Nature, Jul. 2, 2012, 12 pages.
GenBank Accession No. P04626, ERBB2_Human, Found in https://urldefense.com/v3/___https://www.uniprot.org/uniprot/P04626___; IINROYQQILhxStArXEtsYTQ9XizOTbktBixoYuzAr7zjls8adla9Zj-agQd3Pvt1b-yx59evbpbV_$, UniProtKB, Last Sequence Update: Aug. 13, 1987; Last Modified: Apr. 7, 2021, 18 pages.

* cited by examiner

FIG. 1

- A19's binding to various ovarian cancer cell lines

| CLONE | Class | I | | | | II | | | | III | | | | IV | | | |
|---|---|---|---|---|---|---|---|---|---|---|---|---|---|---|---|---|---|
| | | CaOV3 | OVCAR3 | OVCAR8 | OV90 | IGROV-1 | OV17R | OVCA432 | OVCA433 | CH1 | HEY | HEY C2 | SKOV3 | A2780 | HEY A8 | OVCAR10 | TOV112D |
| A19 | IgG1 | 2 | 4 | 4 | 0 | 1 | 0 | 1 | 0 | 0 | 2 | 0 | 4 | 1 | 1 | 0 | 0 |

- A19's binding to various breast cancer cell lines

| CLONE | Class | Cell Lines | | | | | | |
|---|---|---|---|---|---|---|---|---|
| | | MCF7 | T47D | CAMA1 | MDA-MB-231 | HS578T | hME1 | MCF10A |
| A19 | IgG1 | 3 | 4 | 4 | 3 | 2 | 0 | 0 |

- A19's binding to various colorectal cancer cell lines

| CLONE | Class | Cell Lines | | | | | | | | | | | | | | |
|---|---|---|---|---|---|---|---|---|---|---|---|---|---|---|---|---|
| | | COLO205 | SW620 | HT29 | HCT116 | LS174T | HCT15 | KM12 | HCC2998 | RKO | DLD1 | LOVO | SW480 | SKCO1 | SW1116 | CRL1541 |
| A19 | IgG1 | 4 | 0 | 3 | 2 | 1 | 3 | 0 | 1 | 3 | 4 | 3 | 0 | 1 | 0 | 2 |

- A19's binding to NPC

| CLONE | Class | Cell Lines |
|---|---|---|
| | | C666-1 |
| A19 | IgG1 | 3 |

Binding Via FACS

4 Binding > 80%
3 60% < Binding< 80%
2 40% < Binding < 60%
1 20% < Binding < 40%
0 Binding < 20%

(SEQ ID NO: 11)

MPRGSWKPQVCTGTDMKLRLPASPETHLDMLRHLYQGCQVVQGNLELTYLPTNASLSFLQDIQEVQGYVLIAHNQ
VRQVPLQRLRIVRGTQLFEDNYALAVLDNGDPLNNTTPVTGASPGGLRELQLRSLTEILKGGVLIQRNPQLCYQD
TILWKDIFHKNNQLALTLIDTNRSRACHPCSPMCKGSRCWGESSEDCQSLTRTVCAGGCARCKGPLPTDCCHEQ
CAAGCTGPKHSDCLACLHFNHSGICELHCPALVTYNTDTFESMPNPEGRYTFGASCVTACPYNYLSTDVGSCTLV
CPLHNQEVTAEDGTQRCEKCSKPCARVCYGLGMEHLREVRAVTSANIQEFAGCKKIFGSLAFLPESFDGDPASNTA
PLQPEQLQVFETLEEITGYLYISAWPDSLPDLSVFQNLQVIRGRILHNGAYSLTLQGLGISWLGLRSLRELGSGL
ALIHHNTHLCFVHTVPWDQLFRNPHQALLHTANRPEDECVGEGLACHQLCARGHCWGPGPTQCVNCSQFLRGQE
CVEECRVLQGLPREYVNARHCLPCHPECQPQNGSVTCFGPEADQCVACAHYKDPPFCVARCPSGVKPDLSYMPIWK
FPDEEGACQPCPINCTHSCVDLDDKGCPAEQRASPLTSIISAVVGILLVVVLGVVFGILIKRRQQKIRKYTMRRL
LQETELVEPLTPSGAMPNQAQMRILKETELRKVKVLGSGAFGTVYKGIWIPDGENVKIPVAIKVLRENTSPKANK
EILDEAYVMAGVGSPYVSRLLGICLTSTVQLVTQLMPYGCLLDHVRENRGRLGSQDLLNWCMQIAKGMSYLEDVR
LVHRDLAARNVLVKSPNHVKITDFGLARLLDIDETEYHADGGKVPIKWMALESILRRRFTHQSDVWSYGVTVWEL
MTFGAKPYDGIPAREIPDLLEKGERLPQPPICTIDVYMIMVKCWMIDSECRPRFRELVSEFSRMARDPQRFVVIQ
NEDLGPASPLDSTFYRSLLEDDDMGDLVDAEEYLVPQQGFFCPDPAPGAGGMVHHRHRSSSTRSGGGDLTLGLEP
SEEEAPRSPLAPSEGAGSDVFDGDLGMGAAKGLQSLPTHDPSPLQRYSEDPTVPLPSETDGYVAPLTCSPQPEYV
NQPDVRPQPPSPREGPLPAARPAGATLERPKTLSPGKNGVVKDVFAFGGAVENPEYLTPQGGAAPQPHPPPAFSP
AFDNLYYWDQDPPERGAPPSTFKGTPTAENPEYLGLDVPV a.a. length = 1240
(n=5, 38.5% coverage)

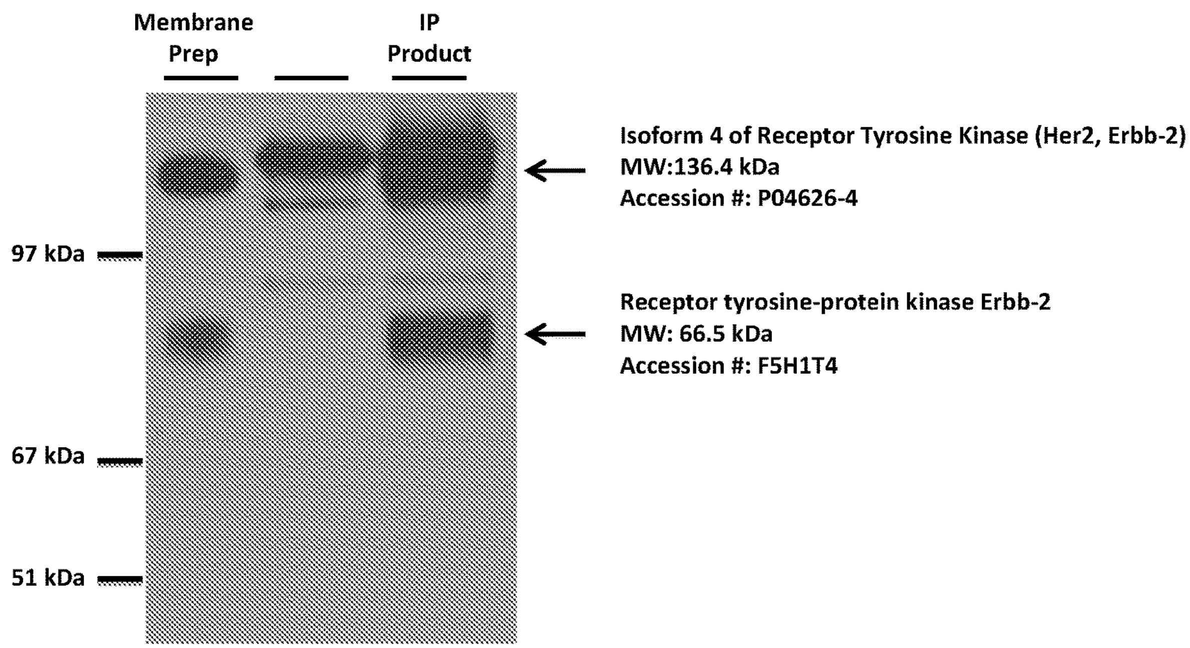

MKLRLPASPETHLDMLRHLYQGCQVVQGNLELTYLPTNASLSFLQDIQEVQGYVLIAHNQVRQVPLQRLRIVRGTQ
LFEDNYALAVLDNGDPLNNTTPVTGASPGGLRELQLRSLTEILKGGVLIQRNPQLCYQDTILWKDIFHKNNQLALT
LIDTNRSRACHPCSPMCKGSRCWGESSEDCQSLTRTVCAGGCARCKGPLPTDCCHEQCAAGCTGPKHSDCLACLHF
NHSGICELHCPALVTYNTDTFESMPNPEGRYTFGASCVTACPYNYLSTDVGSCTLVCPLHNQEVTAEDGTQRCEKC
SKPCARVCYGLGMEHLREVRAVTSANIQEFAGCKKIFGSLAFLPESFDGDPASNTAPLQPEQLQVFETLEEITGYL
YISAWPDSLPDLSVFQNLQVIRGRILHNGAYSLTLQGLGISWLGLRSLRELGSGLALIHHNTHLCFVHTVPWDQLF
RNPHQALLHTANRPEDECVGEGLACHQLCARGHCWGPGPTQCVNCSQFLRGQECVEECRVLQGLPREYVNARHCLP
CHPECQPQNGSVTCFGPEADQCVACAHYKDPPFCVARCPSGVKPDLSYMPIWKFPDEEGACQPCPINCTHS a.a. length = 603
(n=3, 14.3% coverage)

(SEQ ID NO: 12)

Legend
LP: Lipofectamine
SC: Scramble
KD: Knocked Down

Fig. 14
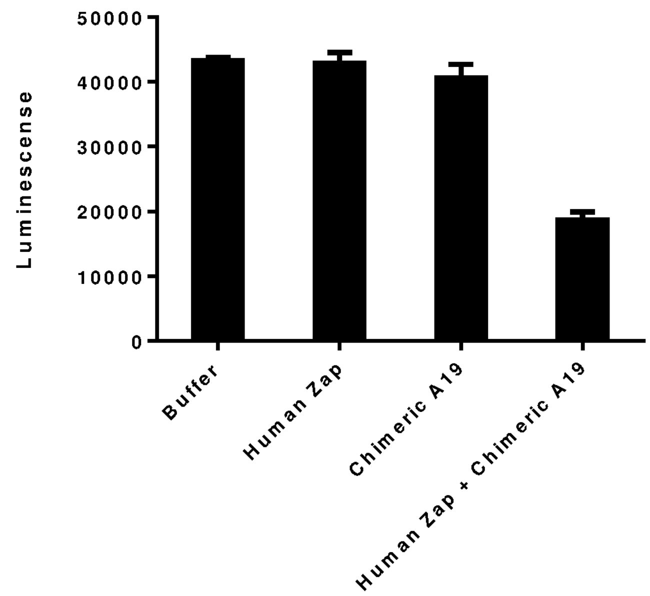
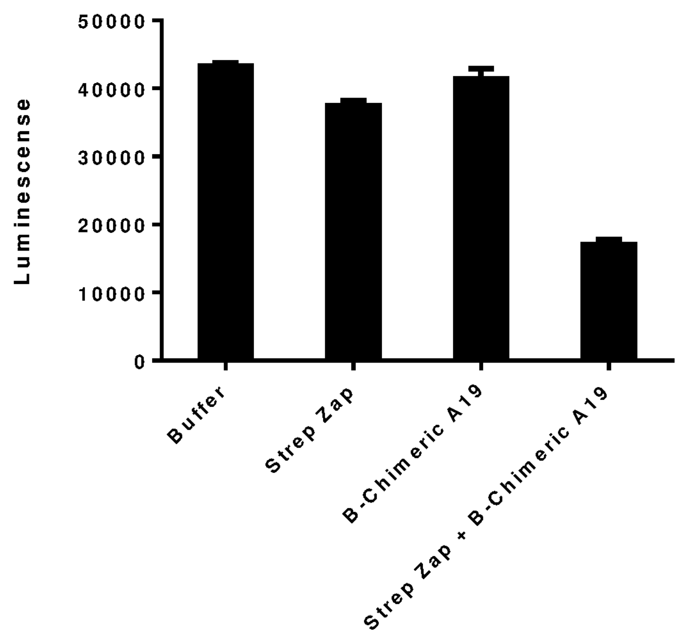

mA19 binding to various cancers

Fig. 19
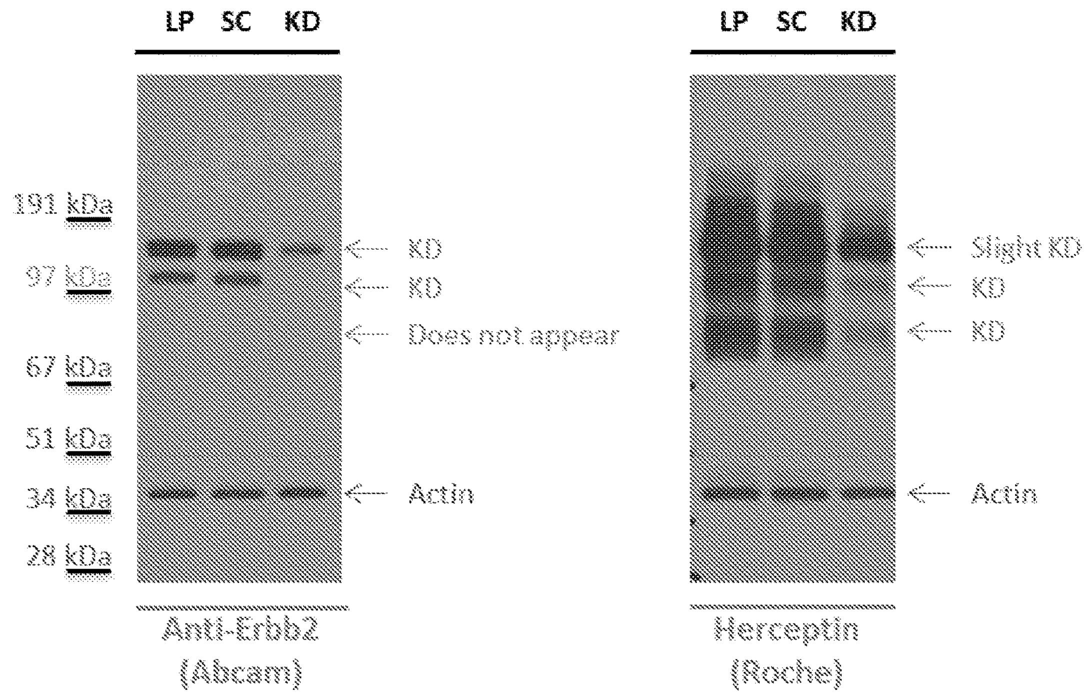
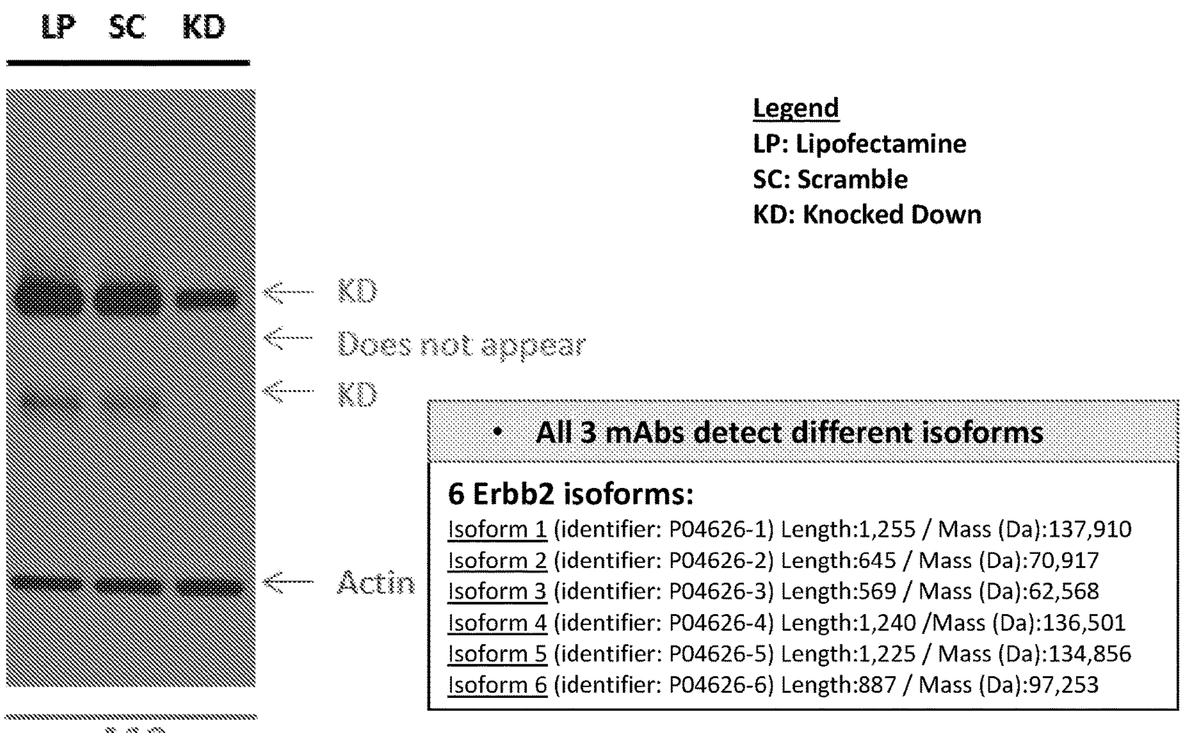

Fig. 20

Variable Gene Sequence

A19 Heavy Chain

Gene Sequence (SEQ ID NO: 9)

CAGGTGAAGCTGCAGGAGTCTGGAGCTGAGCTGATGAAGCCTGGGGCCTCAGTGAAGATATCCTG
CAAGGCTACTGGCTACACATTCAGTAACTACTGGATAGAGTGGGTAAAGCAGAGGCCTGGACATGG
CCTTGAGTGGATTGGAGAGATTTTACCTGGAAGTGATAGTACTAACTACAATGAGAAGTTCAAGGG
CAAGGCCACATTCACTGCAGATACATCCTCCAACACAGCCTACATGCAACTCAGCAGCCTGACATCT
GAGGACTCTGCCGTCTATTACTGTGCAAGAGGAGGGTCGAACTACGGGTACTACTTTGACTACTGG
GGCCAAGGGACCACGGTCACCGTCTCCTCA

A19 Light Chain

Gene Sequence (SEQ ID NO: 10)

GACATTCTGATGACCCAGTCTCACAAATTCATGTCCACATCAGTAGGAGACAGGGTCAGCATCCC
CTGCAAGGCCAGTCAGGATGTGGGTACTGCTGTAGCCTGGTATCAACAAAAACCAGGGCAATCTC
CTAAACTACTGATTTACTGGGCATCCACCCGGCACACTGGAGTCCCTGATCGCTTCACAGGCAGT
GGATCTGGGACAGATTTCACTCTCTCCATTAGCAATGTGCAGTCTGAAGACTTGGCAGATTATTTC
TGTCAGCAATATAGCAGCTATCGGACGTTCGGTGGAGGCACCAAGCTGGAAATCAAACGG

Protein Sequence

A19 Heavy Chain

Protein Sequence (SEQ ID NO: 1)

QVKLQESGAELMKPGASVKISCKATGYTFSNYWIEWVKQRPGHGLEWIGEILPGSDSTNYNEKF
KGKATFTADTSSNTAYMQLSSLTSEDSAVYYCARGGSNYGYYFDYWGQGTTVTVSS

A19 Light Chain

Protein Sequence (SEQ ID NO: 2)

DILMTQSHKFMSTSVGDRVSIPCKASQDVGTAVAWYQQKPGQSPKLLIYWASTRHTGVPDRFTGSGSG
TDFTLSISNVQSEDLADYFCQQYSSYRTFGGGTKLEIKR

ANTI-ERBB-2 ANTIBODIES AND USES THEREOF

CROSS-REFERENCE TO RELATED APPLICATIONS

This patent application is a U.S. National Phase Application Under 35 U.S.C. § 371 of International Application No. PCT/SG2017/050253, filed on 12 May 2016, entitled ANTI-ERBB-2 ANTIBODIES AND USES THEREOF, which claims the benefit of priority of Singapore application number 10201603812X, filed 12 May 2016, the contents of which were incorporated by reference in the entirety for all purposes.

INCORPORATION BY REFERENCE

This patent application incorporates by reference the material (i.e., Sequence Listing) in the ASCII text file named 9322P143_Seq_List.txt, created on Nov. 12, 2018, having a file size of 24,576 bytes.

FIELD OF THE INVENTION

The present invention relates generally to antibodies. Specifically, the present invention relates to anti-ERBB2 antibodies and their uses thereof.

BACKGROUND OF THE INVENTION

Antibody-based therapy has in recent years become an important treatment strategy for cancer. Such therapy functions through mediating alterations in antigen or receptor function, modulating the immune system or delivering a specific drug that is conjugated to an antibody that targets a specific antigen.

The fundamental basis of antibody-based cancer therapy is the fact that cancerous tissues express an array of antigens that may be overexpressed, selectively expressed or mutated compared to normal, non-cancerous tissue. Antibodies against a specific antigen on a cancerous tissue can be used to target and kill the cancerous tissue.

However, a key challenge in developing candidate therapeutic antibodies for cancer is the identification of antigens suitable for antibody-based therapy. Suitability of an antigen for therapy is dependent on various factors including but not limited to the nature of the antigen (e.g. accessibility, abundance, location of expression on cancerous cells etc.), therapeutic approach, antibody affinity and other pharmacokinetic properties.

ERBB2 receptor tyrosine kinase, also known as HER2, HER2/neu and CD340, belongs to the epidermal growth factor receptor (HER/EGFR/ERBB) family and overexpression of ERBB2 has been detected in various cancers. Currently, some anti-ERBB2 antibodies such as Herceptin® and KADCYLA® are commercially available. However, these available antibodies are costly and have been shown to bind to normal cells. Binding of these available antibodies are also not consistent across cancer cell lines. There is therefore a need to develop novel antibodies against ERBB2 that address the disadvantages of the anti-ERBB2 antibodies that are currently available.

SUMMARY

In one aspect, there is provided an antigen-binding protein, or an antigen-binding fragment thereof, comprising (i) a heavy chain variable domain comprising a VHCDR1 having the amino acid sequence GYTFSNYWIE (SEQ ID NO: 3); a VHCDR2 having the amino acid sequence EILPGSDSTNYNEKFKG (SEQ ID NO: 4), and a VHCDR3 having the amino acid sequence GGSNYGYYFDY (SEQ ID NO: 5); and (ii) a light chain variable domain comprising a VLCDR1 having the amino acid sequence KASQDVGTAVA (SEQ ID NO: 6), a VLCDR2 having the amino acid sequence WASTRHT (SEQ ID NO: 7), and a VLCDR3 having the amino acid sequence QQYSSYRT (SEQ ID NO: 8).

In one aspect, there is provided an antigen-binding protein or an antigen-binding fragment thereof, that competes with the antigen binding protein as disclosed herein for binding to ErbB2 receptor protein kinase.

In one aspect, there is provided an antigen-binding protein, or an antigen-binding fragment thereof as disclosed herein comprising a radioisotope or a cytotoxin conjugated thereto.

In one aspect, there is provided a composition comprising a physiologically acceptable carrier and a therapeutically effective amount of the antigen-binding protein, or an antigen-binding fragment thereof as disclosed herein.

In one aspect, there is provided a use of an antigen-binding protein, or an antigen-binding fragment thereof as disclosed herein in the manufacture of a medicament for treating cancer.

In one aspect, there is provided a method for detecting cancer in a subject, the method comprising: contacting a sample obtained from the subject with an antigen-binding protein, or an antigen-binding fragment thereof as disclosed herein in vitro; detecting the binding of the antigen-binding protein, or antigen-binding fragment thereof in the sample; correlating the binding with a level of binding in a control sample to determine the level of binding in the sample, wherein an increase in the level of binding in the sample relative to the control sample is indicative of cancer.

In one aspect, there is provided a kit when used in the method as disclosed herein, comprising an antigen-binding protein or an antigen-binding fragment thereof as disclosed herein, together with instructions for use.

DEFINITIONS

The terms "ERBB2 tyrosine kinase receptor" and "ERBB2" are used interchangeably, and include variants, isoforms, species homologs of ERBB2 tyrosine kinase receptor and analogs having at least one common epitope with ERBB2 receptor tyrosine kinase. Estrogen Related Receptor Beta (ERBB2) is also known in the art as cluster of differentiation 340 (CD340), human epidermal growth factor receptor 2 (HER2) or Neu.

The term "immune response" refers to the action of, for example, lymphocytes, antigen presenting cells, phagocytic cells, granulocytes, and soluble macromolecules produced by the above cells or the liver (including antibodies, cytokines, and complements) that results in selective damage to, destruction of, or elimination from the human body of invading pathogens, cells or tissues infected with pathogens, cancerous cells, or, in cases of autoimmunity or pathological inflammation, normal human cells or tissues.

The term "antigen binding protein" as used herein refers to whole antibodies, antibody fragments (i.e., "antigen-binding portion") and other protein constructs, such as domains, or single chains thereof which are capable of binding to an antigen.

The term "antibody" is used herein in the broadest sense to refer to molecules with an immunoglobulin-like domain and includes monoclonal, recombinant, polyclonal, chimeric, humanised, bispecific and heteroconjugate antibodies; a single variable domain, a domain antibody, antigen binding fragments, immunologically effective fragments, single chain Fv, diabodies, Tandabs™, etc (for a summary of alternative "antibody" formats see Holliger and Hudson, Nature Biotechnology, 2005, Vol 23, No. 9, 1126-1136).

An "antibody" also refers to a glycoprotein comprising at least two heavy (H) chains and two light (L) chains inter-connected by disulfide bonds, or an antigen-binding portion thereof. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "antigen-binding fragment" of an antibody, as used herein, refers to one or more fragments of an antibody that retain the ability to specifically bind to an antigen (e.g., ERBB2 tyrosine kinase receptor). It has been shown that the antigen-binding function of an antibody can be performed by fragments of a full-length antibody. Examples of binding fragments encompassed within the term "antigen-binding fragment" of an antibody include (i) a Fab fragment, a monovalent fragment consisting of the VL, VH, CL and CH1 domains; (ii) a $F(ab')_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR).

The terms "monoclonal antibody" or "monoclonal antibody composition" as used herein refer to a preparation of antibody molecules of single molecular composition. A monoclonal antibody composition displays a single binding specificity and affinity for a particular epitope.

The term "humanized antibody" is intended to refer to antibodies in which CDR sequences derived from the germline of another mammalian species, such as a mouse, have been grafted onto human framework sequences. Additional framework region modifications may be made within the human framework sequences.

The term "chimeric antibody" is intended to refer to antibodies in which the variable region sequences are derived from one species and the constant region sequences are derived from another species, such as an antibody in which the variable region sequences are derived from a mouse antibody and the constant region sequences are derived from a human antibody.

The term "high affinity" for an antibody refers to an antibody having a $K_D$ of $10^{-7}$ or less, $10^{-8}$ M or less, more preferably $10^{-9}$ M or less and even more preferably $10^{-10}$ M or less for a target antigen.

As used herein, the term "subject" includes any human or nonhuman animal. The term "nonhuman animal" includes all vertebrates, e.g., mammals and non-mammals, such as nonhuman primates, sheep, dogs, cats, horses, cows, chickens, amphibians, reptiles, etc. Except when noted, the terms "patient" or "subject" are used interchangeably.

BRIEF DESCRIPTION OF THE DRAWINGS

The invention will be better understood with reference to the detailed description when considered in conjunction with the non-limiting examples and the accompanying drawings, in which:

FIG. 1. Binding of A19 to various cancer cell lines. Membrane staining of tumor cells and FACS staining on live cells was performed. The cells were incubated with A19 on ice for 45 mins, washed and stained with secondary FITC. The binding of A19 is analysed by flow cytometry and binding is based on the population shift from the negative control.

FIG. 3. MS peptide coverage. Peptide sequences from MS were mapped against the protein sequences of Isoform 4 of Receptor Tyrosine Kinase (Her2, Erbb-2) (top sequence) and Receptor tyrosine-protein kinase Erbb-2 (bottom sequence).

FIG. 6 shows A19 and Herceptin binds to glycans. The cell line used was SKOV3.

FIG. 7 shows that A19 and Herceptin bind to N-linked glycans. The cell line used was SKOV3.

FIG. 8 shows that A19 and Herceptin do not bind to O-linked glycans.

FIG. 9 shows that chimeric A19 does not elicit ADCC.

FIG. 10 shows that naked A19 has no effect on cell growth in vitro.

FIG. 11 shows that naked A19 has no effect on cell growth in vitro.

FIG. 12 shows that chimeric A19 internalizes into cells.

FIG. 14. A19 can be used as an antibody-drug conjugate (ADC). A19 is conjugated to the toxin saporin via a secondary mAb or via streptavidin-biotin affinity. As an ADC, A19 kills cells in vitro. The cell line used was SKOV3. FIG. 14 shows that chimeric A19 can be used as ADC.

FIG. 15 shows that ADC is observed on other cancers and that a significant ADC effect is observed on cell lines that highly express Erbb-2 whilst there is a slight effect on COLO205.

FIG. 16 shows that A19 works as an ADC. Naked A19 (5 mg/ml) has no effect on cell proliferation.

FIG. 17 shows that A19 works as an ADC in vivo although conjugation is sub-optimal. The cell line used was SKOV3. There was no animal model for MCF7.

FIG. 18 shows that chimeric A19 does not bind to the same epitope as Herceptin. The cell line used was SKOV3.

FIG. 19. Isoforms that the monoclonal antibodies (mAbs) detect. All 3 mAbs detect various isoforms of Erbb-2. The isoform that is probably common to the 3 mAbs is the upper band or isoform 4. FIG. 19 shows that A19's antigen target is Erbb-2/Her2.

FIG. 20. Variable gene sequence and protein sequence of A19. Variable gene sequences of the A19 heavy (SEQ ID NO: 9) and light chains (SEQ ID NO: 10) and the protein sequence of the A19 heavy (SEQ ID NO: 1) and light chains (SEQ ID NO: 2) are shown.

DETAILED DESCRIPTION OF THE PRESENT INVENTION

Figure 2:
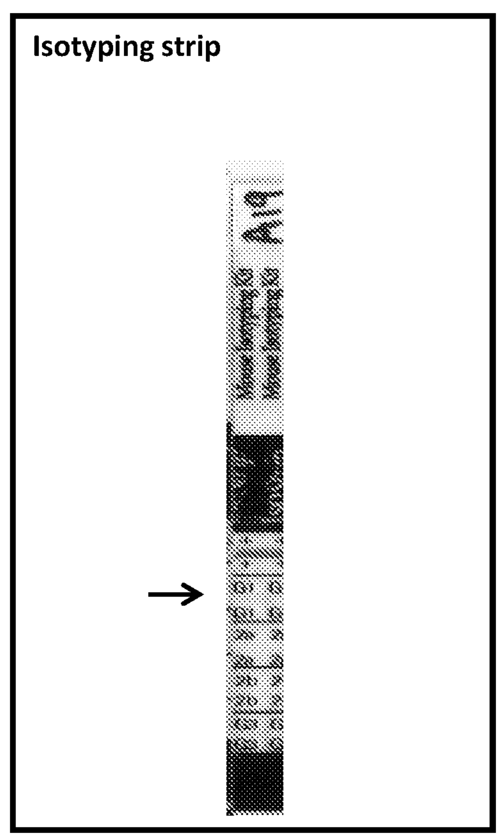
FIG. 2. A) Isotyping of A19. Isotyping was carried out with Roche isotyping strip. B) Identification of target antigen. IP on SKOV3 membrane preparation was carried out, followed by western blot. The corresponding band was excised from a parallel SDS Page gel and the antigen target identified via MS. A19 is: an IgG1; has 2 distinct bands of different molecular weights; isotyping/immunoprecipitation-Mass Spectrometry (IP/MS) was performed on both bands.
Figure 2:
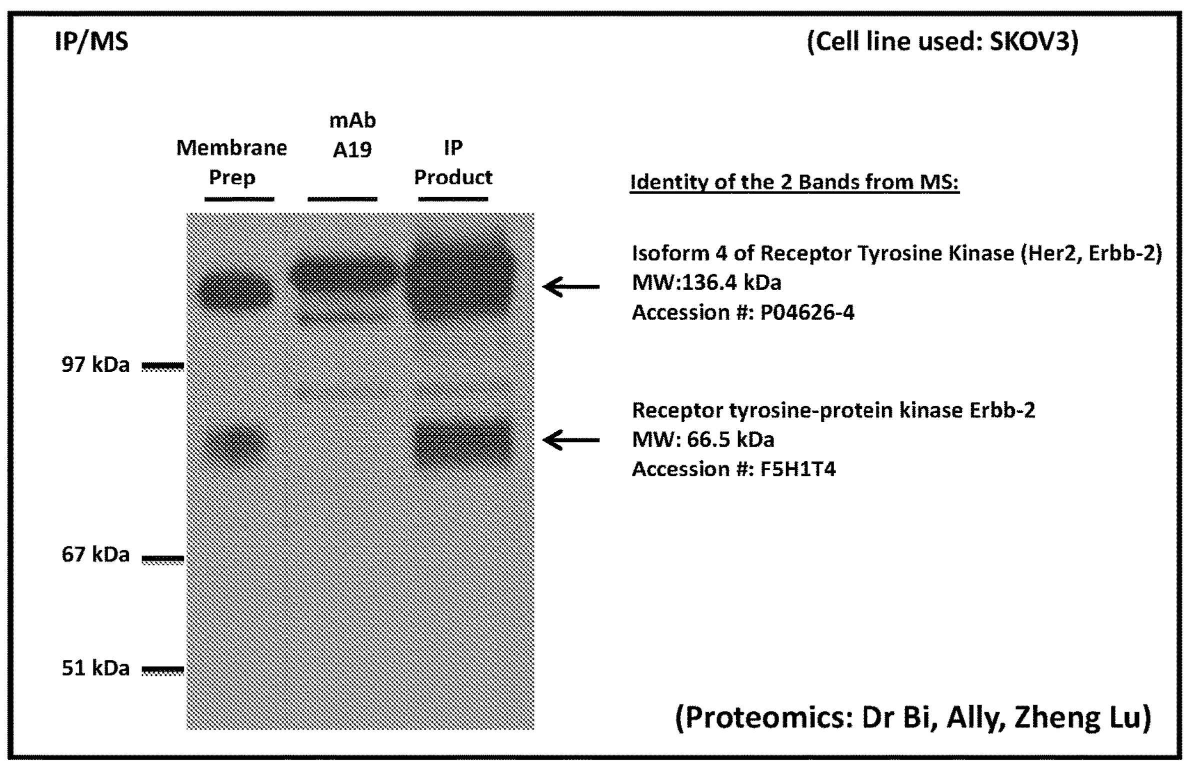
Figure 4:
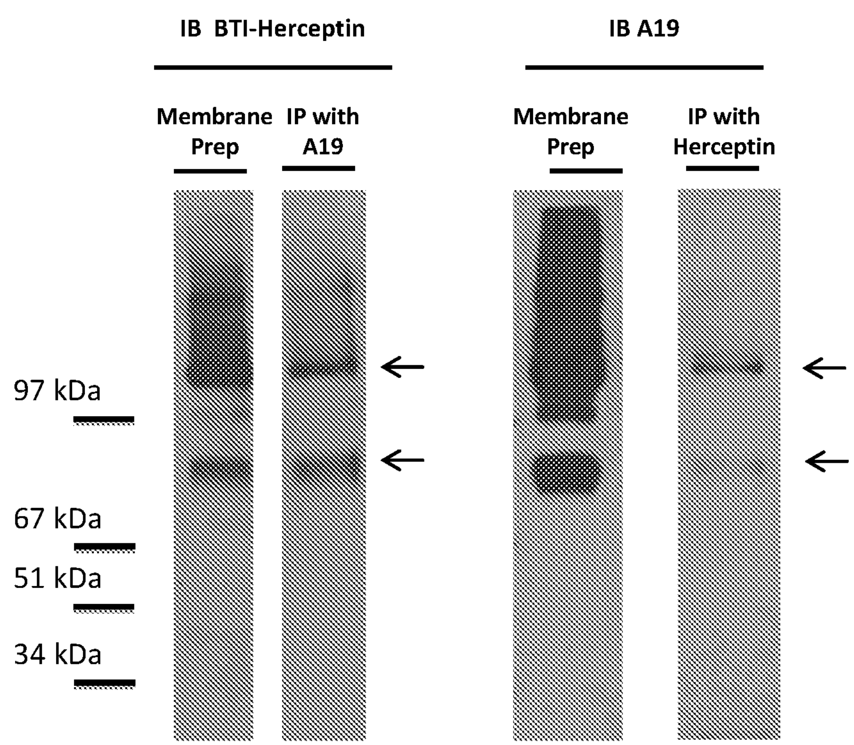
FIG. 4. Validation of identity via cross probing. Immunoprecipitation (IP) was carried out with A19 and immunoblotted with Herceptin. Similarly, IP was carried out with Herceptin and immunoblotted with A19. In both experiments, the same antigen was detected confirming that the antigen target of A19 is Erbb-2. The same antigens were detected in both sets of IP. The cell line used was SKOV3.
Figure 5:
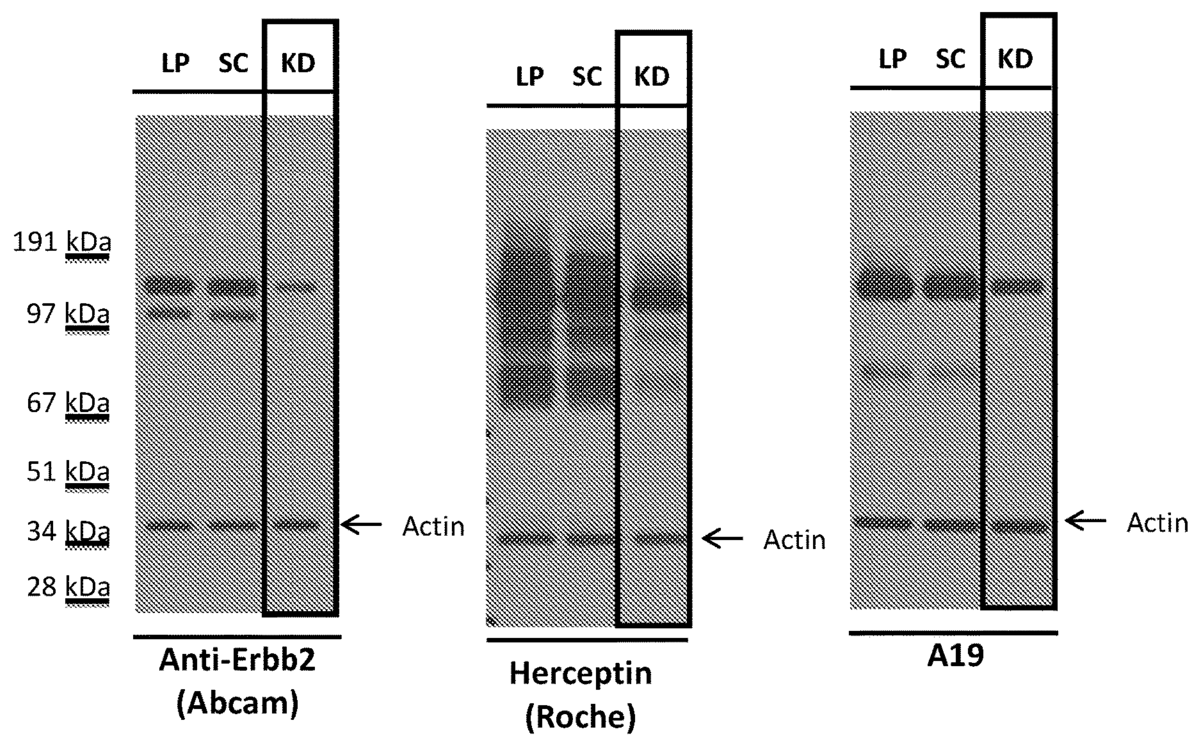
FIG. 5. Validation of identity via knock down with siRNA. Knocked down of Erbb-2 was carried out using siRNA. Via western blot, all three antibodies to Erbb-2 showed diminished binding, confirming that the antigen target is Erbb-2. The cell line used was SKOV3.
Figure 6:
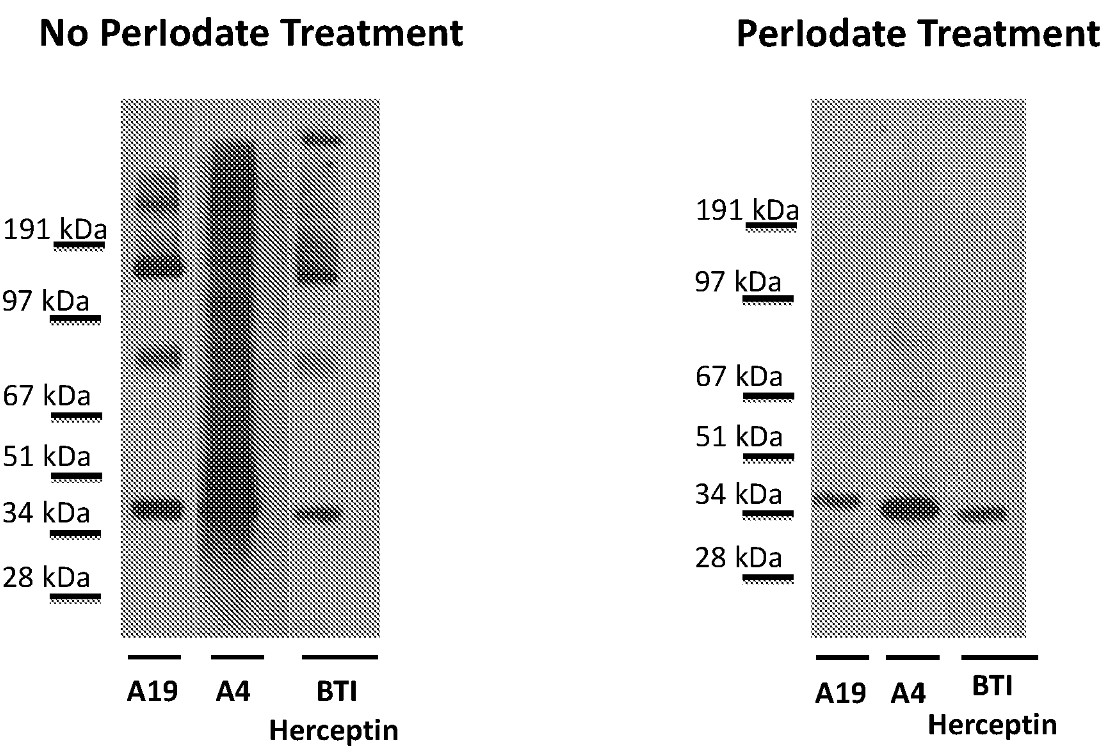
FIG. 6. Glycan analysis. Upon treatment with perlodate, the binding of A19 is abolished. The figure shows actin bands at 39 kDa (protein-binding control) and monoclonal antibody (mAb) A4 as the positive control for perlodate treatment.
Figure 7:
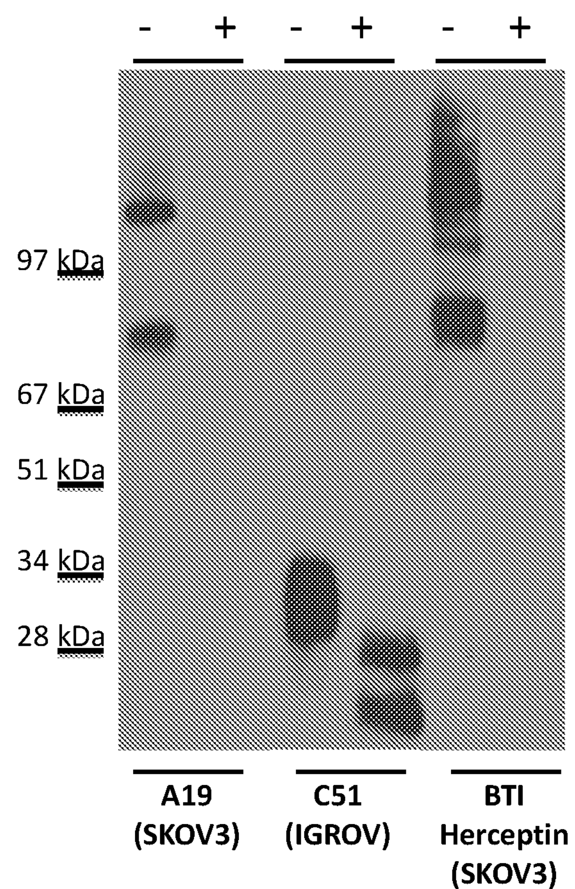
FIG. 7. N-linked glycan analysis. Upon enzymatic removal of N-linked glycans by PNGase, the binding of A19 was abolished.
Figure 8:
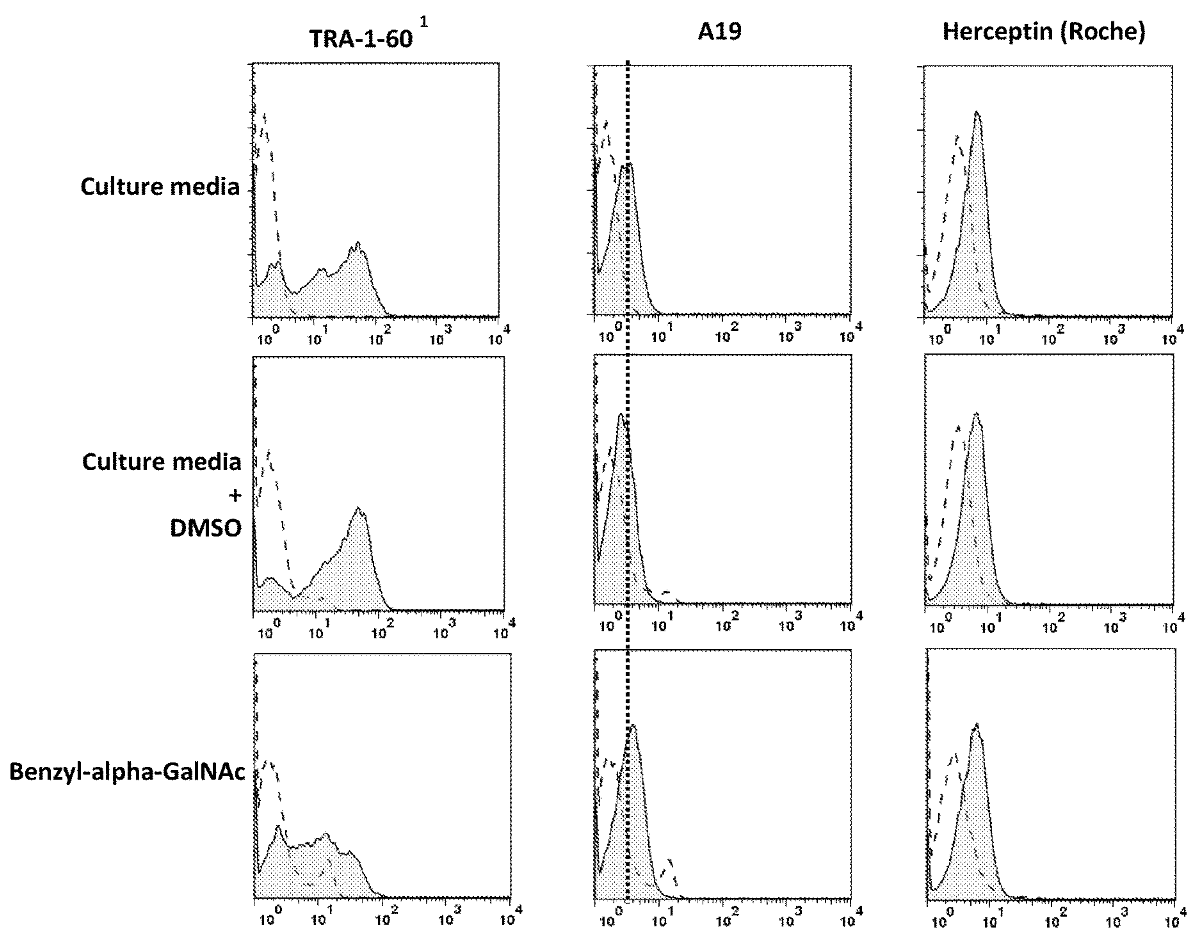
FIG. 8. O-linked glycan analysis. O-linked glycan synthesis was inhibited in culture with Benzyl-alpha-GalNAc. The loss of O-linked glycans was confirmed by the loss of binding of TRA-1-60. Binding of A19 was similar to the control, confirming that the binding of A19 is not to O-linked glycans. The cell line used was HES-3.
Figure 9:
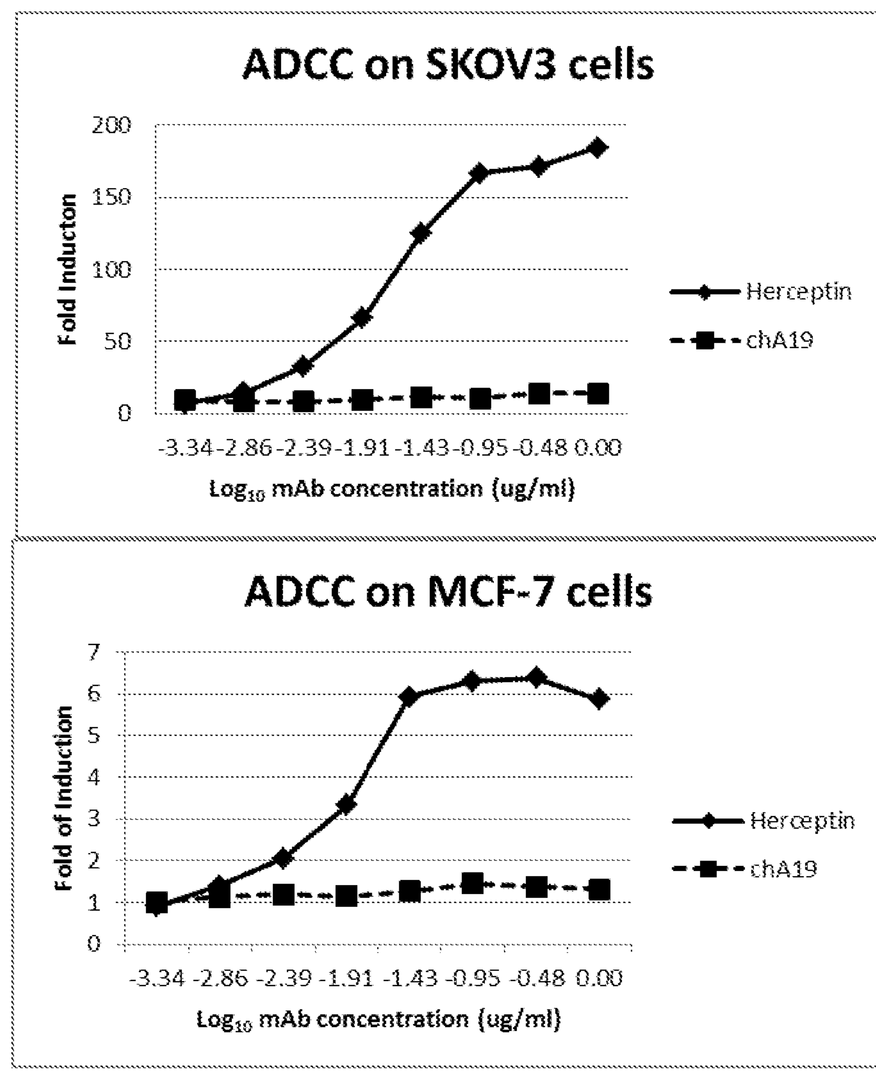
FIG. 9. In vitro ADCC activity of A19. A19 does not exhibit ADCC activity when cultured with either ovarian and breast cancer cells. ADCC activity was measured as fold induction of the NFAT pathway using an ADCC reporter bio-assay (Promega).
Figure 10:
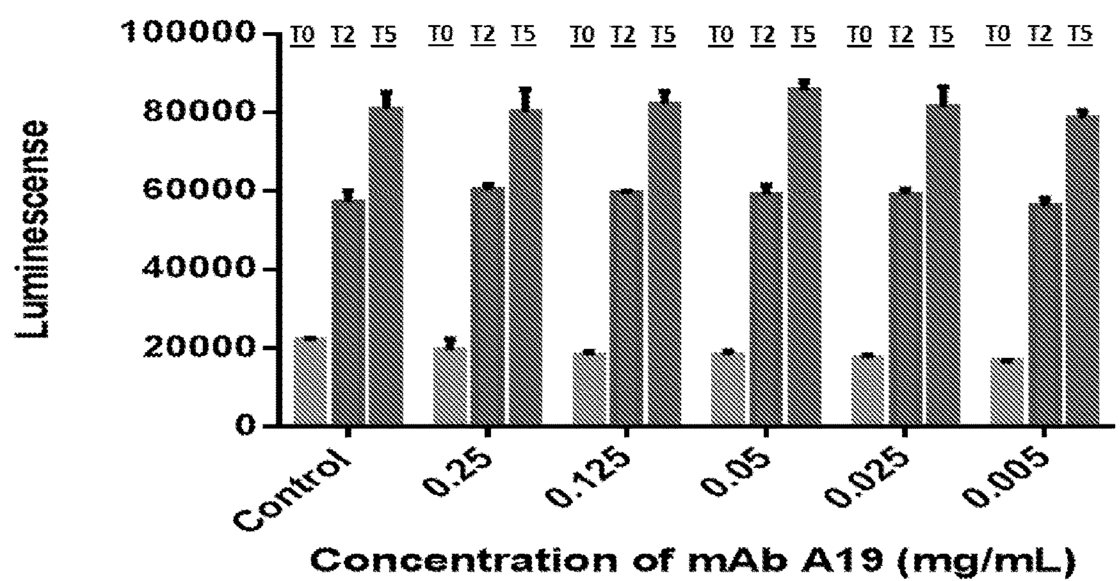
FIG. 10. Bioactivity of naked A19. A19 was spiked into SKOV3 at various doses and viability measured through Cell Titre Glow (CTG) at Day 2 (T2) and Day 5 (T5). The viability of the cells at various doses of A19 was comparable to the control at both T2 and T5. The cell line used was SKOV3.
Figure 11:
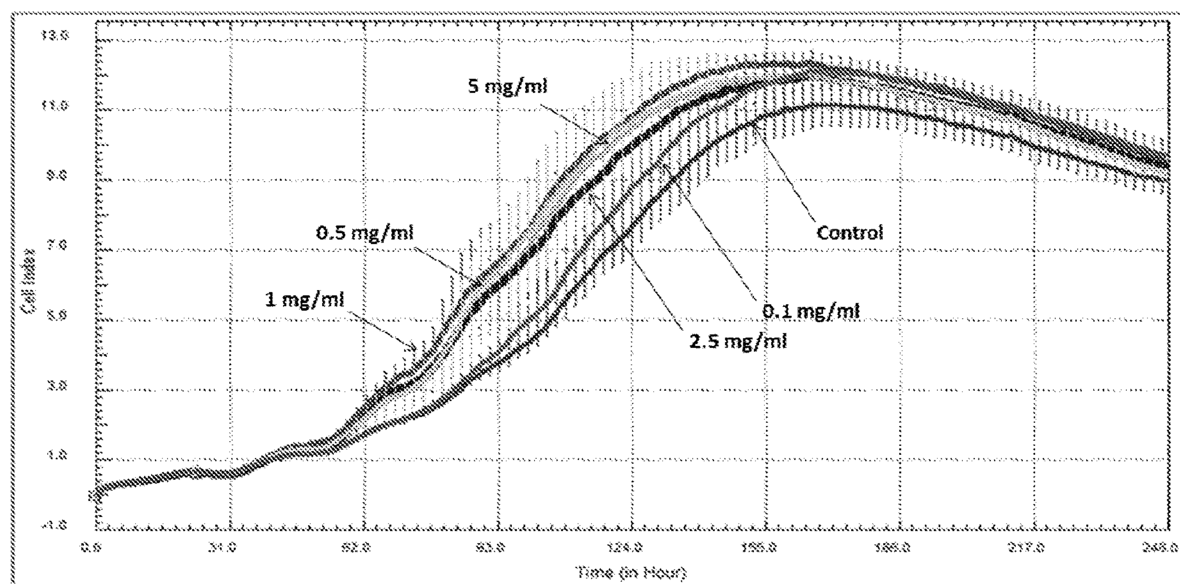
FIG. 11. Bioactivity of naked A19. A19 was spiked into SKOV3 at various doses ranging from 0 to 5 mg/ml and the growth monitored real-time. There is no difference in growth for all doses of A19. The cell line used was SKOV3.
Figure 12:
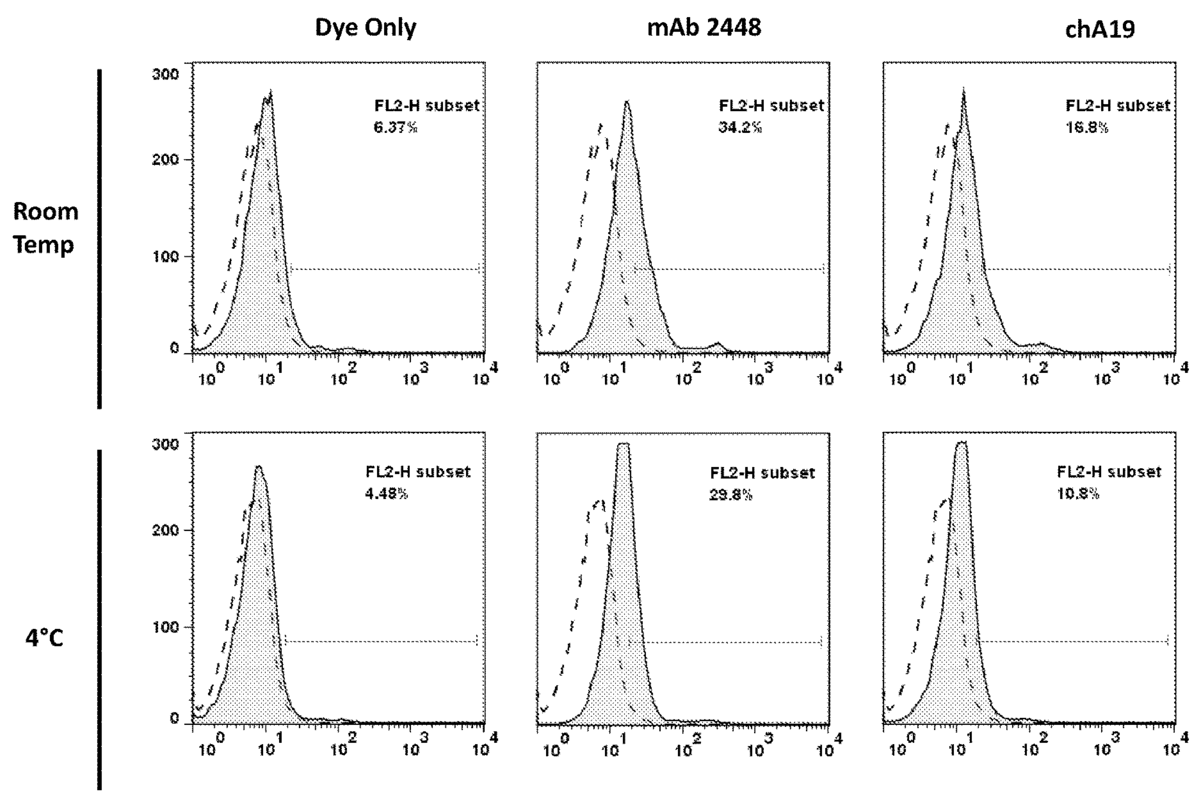
FIG. 12. A19 internalizes into cells. A19 was conjugated to a dye (pHRodo, ThermoFisher Scientific) which fluoresces brightly when the antibody complex enters the cells to an acidic environment. The dotted histogram represents cells not treated with antibodies while the shaded histogram represents cells treated with antibodies. The negative control consist of the pHRodo dye (not conjugated to any antibody), while mAb2448 is a known mAb that internalizes into the cells (positive control). The cell line used was SKOV3.
Figure 13:
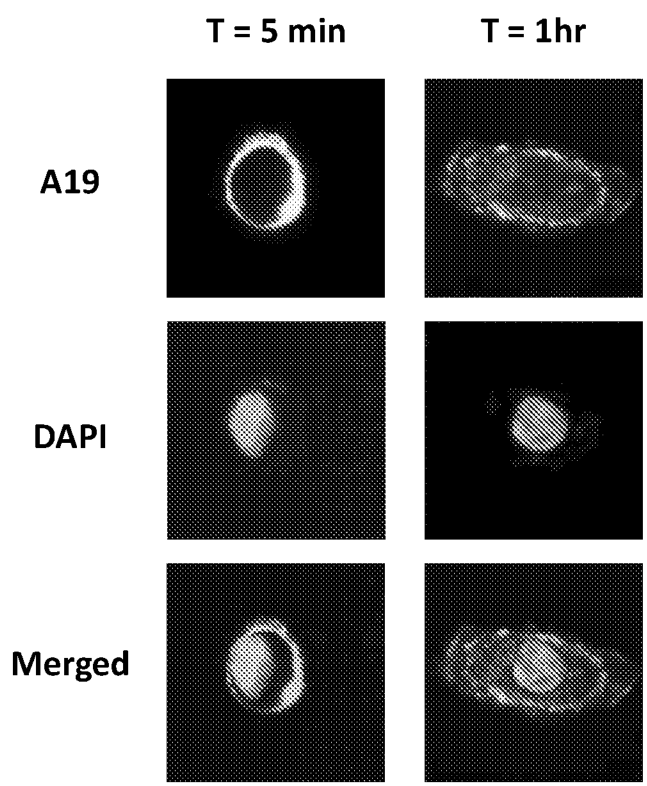
FIG. 13. A19 internalizes into cells. Immuno-staining of A19 at T=5 min shows that the antibody forms a bright ring around the cell. After 1 hr, the antibody internalizes into the cell, as observed by the punctuated and scattered staining of A19 inside the cell. The cell line used was SKOV3.
Figure 15:
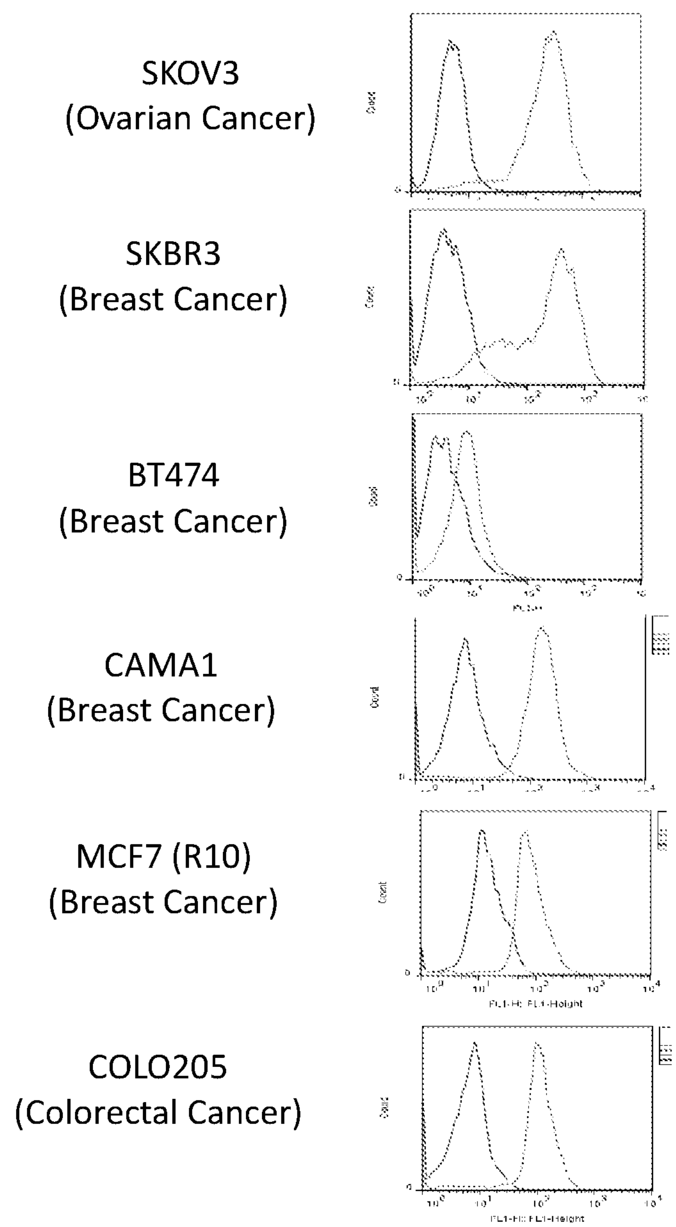
FIG. 15. A19 as an ADC kills cells that highly express Erbb-2. Out of the various cancer cells, SKOV3 and SKBR3 express high levels of Erbb2. A19-ADC has effect only on SKOV3 and SKBR3 in vitro.
Figure 15:
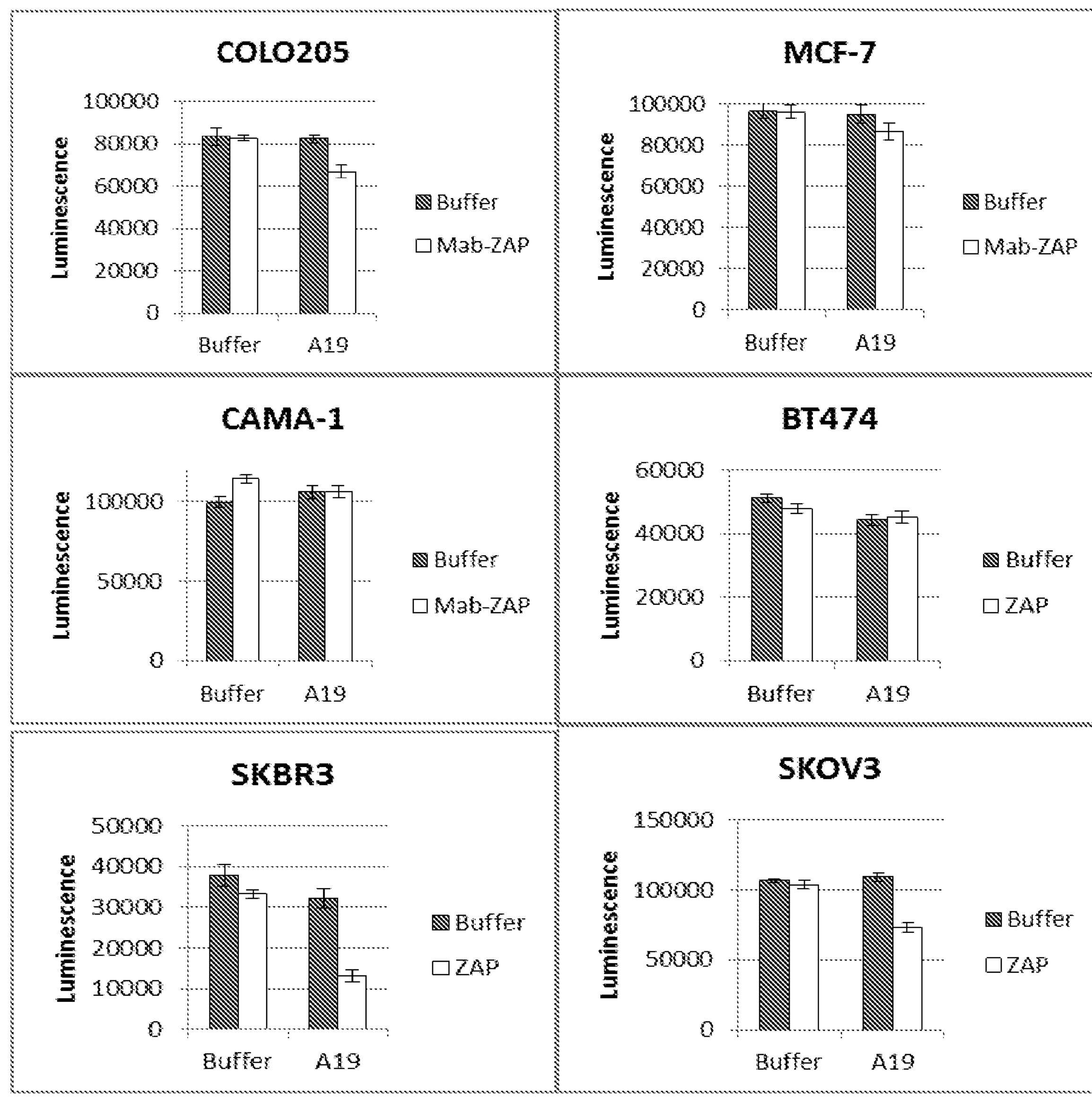
Figure 16:
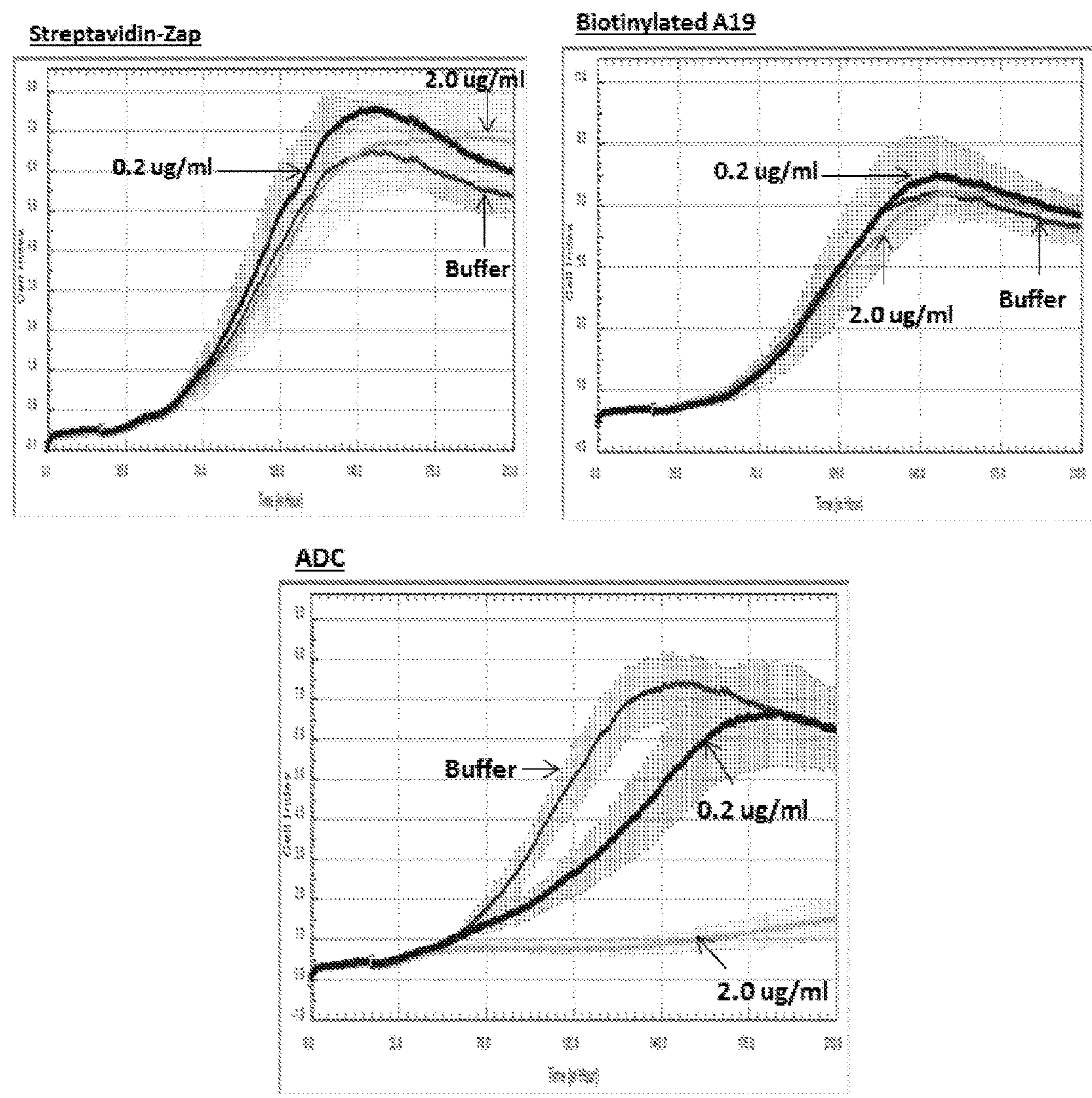
FIG. 16. A19-ADC kills cells in a dosage dependent manner. As an ADC, A19 kills SKOV3 in vitro, in a dose-dependent manner. It is noted that the dosage used is 1000× lower compared to that of naked A19. The cell line used was SKOV3.
Figure 17:
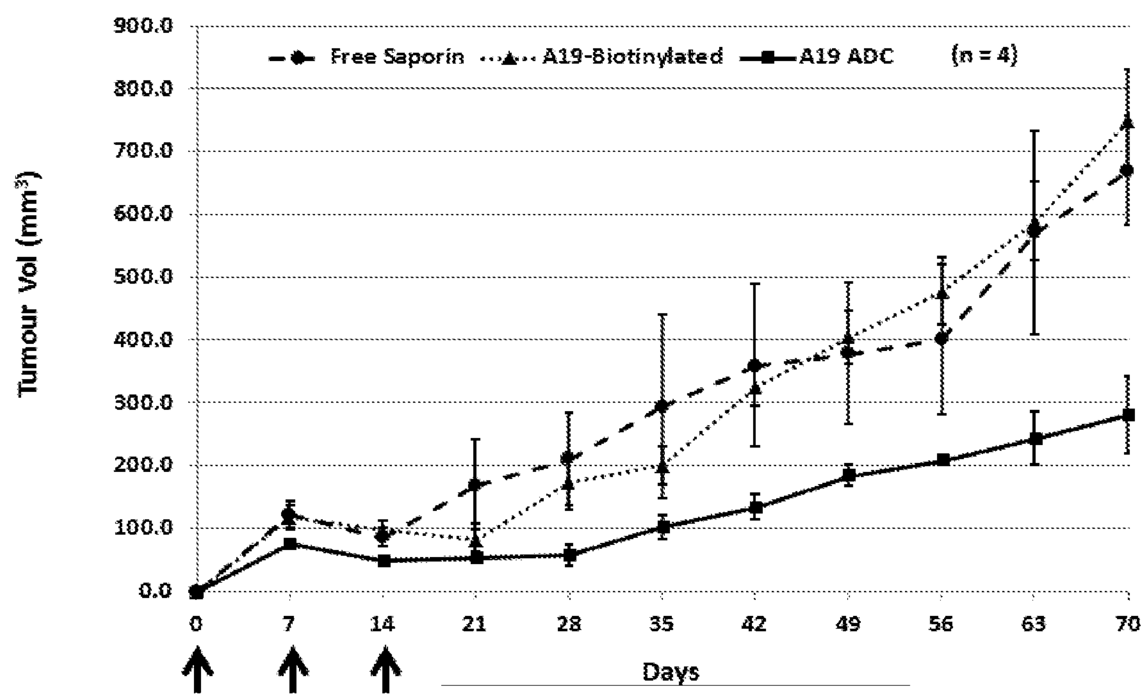
FIG. 17. A19-ADC suppresses tumour growth in vivo. Three doses of A19-ADC (37.5 ug per dose) was administered 1 week apart, intraperitoneally. Tumour size was tracked over 2 months. Cells were injected into the right flank of mice (subcutaneous).
Figure 18:
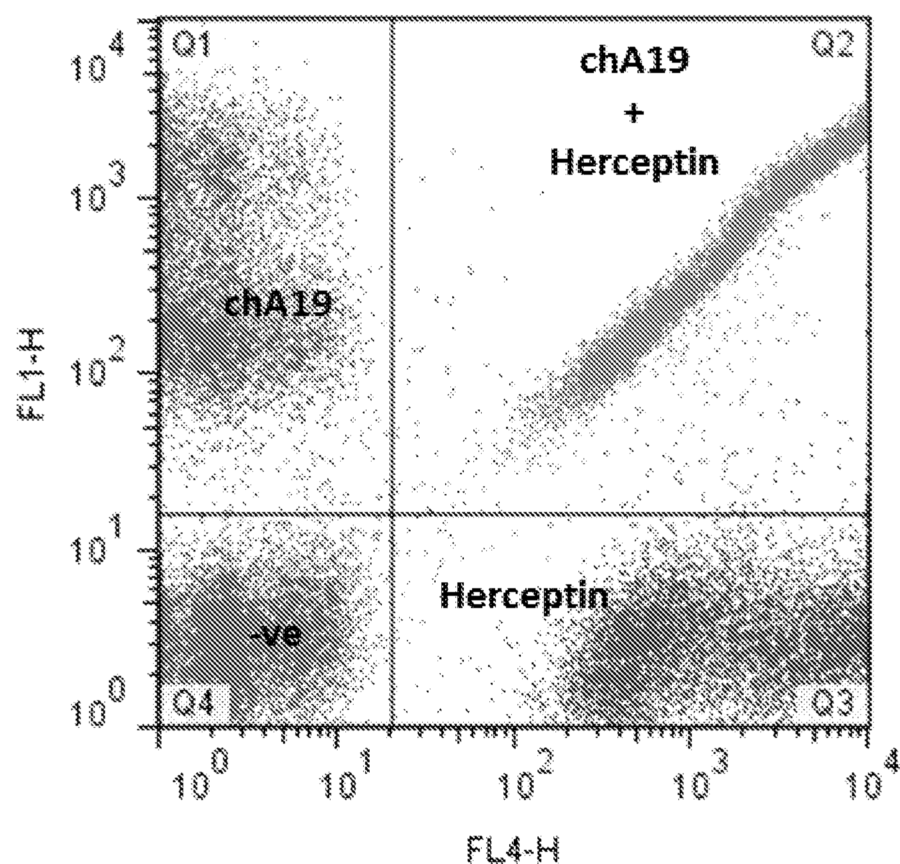
FIG. 18. Competitive binding between A19 and Herceptin. A19 and Herceptin were individually conjugated to Alexafluor 488 and APC respectively. Individual stains showed that the antibodies bind to the cells (Q1 for A19, Q3 for Herceptin). When the antibodies were incubated together, they do not compete with each other (Q2).

In a first aspect the present invention refers to an antigen-binding protein, or an antigen-binding fragment thereof, comprising (i) a heavy chain variable domain comprising a VHCDR1 having the amino acid sequence GYTFSNYWIE (SEQ ID NO: 3); a VHCDR2 having the amino acid sequence EILPGSDSTNYNEKFKG (SEQ ID NO: 4), and a VHCDR3 having the amino acid sequence GGSNYGYYFDY (SEQ ID NO: 5); and (ii) a light chain variable domain comprising a VLCDR1 having the amino acid sequence KASQDVGTAVA (SEQ ID NO: 6), a VLCDR2 having the amino acid sequence WASTRHT (SEQ ID NO: 7), and a VLCDR3 having the amino acid sequence QQYSSYRT (SEQ ID NO: 8).

In one embodiment, the antigen-binding protein, or antigen-binding fragment thereof comprises heavy and light chain CDR regions that are about 80%, about 85%, about 90%, about 95%, about 96%, about 97%, about 98% or about 99% identical to SEQ ID NO: 3, SEQ ID NO: 4, SEQ ID NO: 5, SEQ ID NO: 6, SEQ ID NO: 7 and SEQ ID NO: 8.

In a preferred embodiment, the heavy chain variable region of the antigen-binding protein, or antigen-binding fragment thereof as disclosed herein may comprise the amino acid sequence set forth in SEQ ID NO:1.

In one embodiment, the antigen-binding protein, or antigen-binding fragment thereof as disclosed herein may comprise a heavy chain variable region which comprises an amino acid sequence having about 80%, about 85%, about 90%, about 95%, about 96%, about 97%, about 98% or about 99% identity to the amino acid sequence set forth in SEQ ID NO:1.

In another preferred embodiment, the light chain variable region of the antigen-binding protein, or antigen-binding fragment thereof as disclosed herein may comprise the amino acid sequence set forth in SEQ ID NO:2.

In another embodiment, the antigen-binding protein, or antigen-binding fragment thereof as disclosed herein may comprise a light chain variable region which comprises an amino acid sequence having about 80%, about 85%, about 90%, about 95%, about 96%, about 97%, about 98% or about 99% identity to the amino acid sequence set forth in SEQ ID NO:2

As used herein, the percent homology between two amino acid sequences is equivalent to the percent identity between the two sequences. The percent identity between the two sequences is a function of the number of identical positions shared by the sequences (i.e., % homology=# of identical positions/total # of positions ×100), taking into account the number of gaps, and the length of each gap, which need to be introduced for optimal alignment of the two sequences.

In one embodiment, the antigen-binding protein, or antigen-binding fragment thereof as disclosed herein is selected from the group consisting of monoclonal, recombinant, polyclonal, chimeric, humanised, bispecific and heteroconjugate antibodies; a single variable domain, a domain antibody, antigen binding fragments, immunologically effective fragments, single chain Fv, a single chain antibody, a univalent antibody lacking a hinge region, a minibody, diabodies, and Tandabs™.

In a further embodiment, the antigen-binding protein, or antigen-binding fragment thereof is a polyclonal or monoclonal antibody. In a preferred embodiment, the antigen-binding protein, or antigen-binding fragment thereof is a monoclonal antibody.

In a further preferred embodiment, the monoclonal antibody is A19. The monoclonal antibody may be humanized.

The antigen-binding protein, or antigen-binding fragment thereof of the present invention may bind to ERBB2 receptor protein kinase. In some embodiments, the antigen-binding protein, or antigen-binding fragment thereof may bind to one or more isoforms of ERBB2 receptor protein kinase. Examples of isoforms of ERBB2 receptor protein kinase include isoforms 1, 2, 3, 4, 5 and 6. In some embodiments, the isoforms may be truncated. In other embodiments, the antigen-binding protein, or antigen-binding fragment thereof may bind to a truncated isoform 4 of ERBB2 receptor protein kinase. In a further embodiment, the truncated isoform 4 does not comprise any hydrophobic regions.

In some embodiments, the antigen-binding protein, or antigen-binding fragment thereof binds to a glycan on the ERBB2 receptor protein kinase. In some embodiments, the antigen-binding protein, or antigen-binding fragment thereof binds to an extracellular glycan on the ERBB2 receptor protein kinase.

As used herein, glycan refers to a polysaccharide that may be homo- or hetero polymers of monosaccharides. Glycans include N-linked glycans and O-linked glycans. N-linked glycans are glycans whose monosaccharides are linked to the nitrogen in the side chain of asparagine. O-linked glycans are glycans whose monosaccharides are linked on a serine or threonine amino acid reside.

In a preferred embodiment, the antigen-binding protein, or antigen-binding fragment thereof may bind to an N-linked glycan on the ERBB2 receptor protein kinase. In a further preferred embodiment, the N-linked glycan may be located at one or more of amino acid positions 66, 124, 187, 259, 530, 571 and 629 of ERBB2 receptor protein kinase.

In another aspect, the present invention relates to an antigen-binding protein or an antigen-binding fragment thereof that competes with the antigen binding protein as disclosed herein for binding to the same epitope of ERBB2 receptor protein kinase. Competition with respect to binding may refer to binding affinity or to binding mechanism. For example, an antigen-binding protein, or an antigen-binding fragment thereof that competes with the antigen binding protein as disclosed herein for binding to ERBB2 receptor protein kinase may compete by binding to the same ERBB2 epitope with at least the same affinity or with higher affinity. Competitive binding may also be achieved by reducing avidity of binding.

In another aspect, the present invention relates to an antigen-binding protein, or an antigen-binding fragment thereof as disclosed herein conjugated to a therapeutic moiety, such as a cytotoxin, a drug (e.g., an immunosuppressant), a radiotoxin or a radioisotope.

Such conjugates are referred to herein as "immunoconjugates" or "antibody drug conjugates (ADCs)". Immunoconjugates that include one or more cytotoxins are referred to as "immunotoxins." A cytotoxin or cytotoxic agent includes any agent that is detrimental to (e.g., kills) cells. Examples include monomethyl auristatin E (MMEA-1), mertansine (DM-1) and saporin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents also include, for example, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). Other examples of therapeutic cytotoxins that can be conjugated to an antibody of the invention include duocarmycins, calicheamicins, maytansines and auristatins, and derivatives thereof.

In a preferred embodiment, the cytotoxin is selected from the group consisting of monomethyl auristatin E (MMEA-1), mertansine (DM-1) and saporin.

Cytotoxins can be conjugated to antibodies of the invention using linker technology available in the art. Examples of linker types that have been used to conjugate a cytotoxin to an antibody include, but are not limited to, hydrazones, thioethers, esters, disulfides and peptide-containing linkers.

Antibodies of the present invention also can be conjugated to a radioactive isotope to generate cytotoxic radiopharmaceuticals, also referred to as radioimmunoconjugates. Examples of radioactive isotopes that can be conjugated to antibodies for use diagnostically or therapeutically include, but are not limited to, iodine$^{131}$, indium$^{111}$, yttrium$^{90}$ and lutetium$^{177}$. Methods for preparing radioimmunconjugates are established in the art. Examples of radioimmunoconjugates are commercially available, including Zevalin.™ (IDEC Pharmaceuticals) and Bexxar.™. (Corixa Pharmaceuticals), and similar methods can be used to prepare radioimmunoconjugates using the antibodies of the invention.

The antibody conjugates of the invention can be used to modify a given biological response, and the drug moiety is not to be construed as limited to classical chemical therapeutic agents. For example, the drug moiety may be a protein or polypeptide possessing a desired biological activity. Such proteins may include, for example, an enzymatically active toxin, or active fragment thereof, such as abrin, ricin A, pseudomonas exotoxin, or diphtheria toxin; a protein such as tumor necrosis factor or interferon-gamma; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

In some embodiments, the antigen-binding protein, or an antigen-binding fragment comprising a radioisotope or cytotoxin conjugated thereto is internalized into a cell upon binding to ERBB2 receptor tyrosine kinase. Internalization of the antigen-binding protein or antigen-binding fragment comprising a radioisotope or cytotoxin conjugated thereto releases the radioisotope or cytotoxin and may trigger cell death.

In some embodiments, the antigen-binding protein, or an antigen-binding fragment thereof may trigger cell death by antibody-dependent cell-mediated cytotoxicity (ADCC) or complement dependent cytotoxicity (CDC).

In another aspect, the present invention provides a composition comprising a physiologically acceptable carrier and a therapeutically effective amount of the antigen-binding protein, or an antigen-binding fragment thereof as disclosed herein.

Compositions may include one or a combination of (e.g., two or more different) antigen-binding protein, antigen-binding fragment thereof, antibodies, or immunoconjugates or bispecific molecules of the invention. For example, a pharmaceutical composition of the invention can comprise a combination of antibodies (or immunoconjugates or bispecifics) that bind to different epitopes on the target antigen or that have complementary activities.

Pharmaceutical compositions of the invention also can be administered in combination therapy, i.e., combined with other agents. In some embodiments, the compositions of the present invention may comprise a further active pharmaceutical ingredient selected from the group consisting of bevacizumab, carboplatin, paclitaxel or gefitinib. In other embodiments, the compositions of the present invention may be administered with chemotherapy.

As used herein, “pharmaceutically acceptable carrier” or “physiologically acceptable carrier” includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). Depending on the route of administration, the active compound, i.e., antibody, immunoconjugate, or bispecific molecule, may be coated in a material to protect the compound from the action of acids and other natural conditions that may inactivate the compound.

Pharmaceutically acceptable carriers include sterile aqueous solutions or dispersions and sterile powders for the extemporaneous preparation of sterile injectable solutions or dispersion. The use of such media and agents for pharmaceutically active substances is known in the art. Except insofar as any conventional media or agent is incompatible with the active compound, use thereof in the pharmaceutical compositions of the invention is contemplated. Supplementary active compounds can also be incorporated into the compositions.

The pharmaceutical compounds of the invention may include one or more pharmaceutically acceptable salts. A “pharmaceutically acceptable salt” or “physiologically acceptable salt” refers to a salt that retains the desired biological activity of the parent compound and does not impart any undesired toxicological effects. Examples of such salts include acid addition salts and base addition salts. Acid addition salts include those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include those derived from alkaline metals or alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like.

A pharmaceutical composition of the invention also may include a pharmaceutically acceptable anti-oxidant. Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of presence of microorganisms may be ensured both by sterilization procedures, supra, and by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

A composition of the present invention can be administered via one or more routes of administration using one or more of a variety of methods known in the art. As will be appreciated by the skilled artisan, the route and/or mode of administration will vary depending upon the desired results. Preferred routes of administration for antibodies of the invention include intravenous, intramuscular, intradermal, intraperitoneal, subcutaneous, spinal or other parenteral routes of administration, for example by injection or infusion. The phrase “parenteral administration” as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

Alternatively, an antibody of the invention can be administered via a non-parenteral route, such as a topical, epidermal or mucosal route of administration, for example, intranasally, orally, vaginally, rectally, sublingually or topically.

In one aspect, the present invention relates to a use of an antigen-binding protein, or an antigen-binding fragment thereof as disclosed herein in the manufacture of a medicament for treating cancer.

It will be generally understood that cancer treatment includes one or more of inhibiting growth of cancer cells, suppressing proliferation of cancer cells, triggering cell death, and activating host immune response to cancer cells.

Preferred cancers which may be treated using the antigen-binding protein, or antigen-binding fragment thereof as disclosed herein include cancers typically responsive to immunotherapy. Non-limiting examples of preferred cancers for treatment include melanoma (e.g., metastatic malignant melanoma), renal cancer (e.g. clear cell carcinoma), prostate cancer (e.g. hormone refractory prostate adenocarcinoma), breast cancer, colon cancer and lung cancer (e.g. non-small cell lung cancer). Additionally, the invention includes refractory or recurrent malignancies whose growth may be inhibited using the antibodies of the invention.

Examples of other cancers that may be treated using the methods of the invention include bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, the cancer may be selected from a cancer that expresses an epitope that the antigen-binding protein, or an antigen-binding fragment thereof as disclosed herein binds.

In a preferred embodiment, the cancer is selected from breast, colorectal, ovarian, lung, retinoblastoma, gastric, cervical and pancreatic cancer.

In other embodiments, the medicament disclosed herein may be administered with a further active pharmaceutical ingredient.

In yet other embodiments, the medicament disclosed herein may be administered with chemotherapy.

The further active pharmaceutical agent or chemotherapy may be administered separately, simultaneously or sequentially with the medicament, composition, antigen-binding protein, or antigen-binding fragment thereof as disclosed herein. Sequentially as used herein, refers to administration of the further active pharmaceutical agent or chemotherapy before or after administration of the medicament, composition, antigen-binding protein, or antigen-binding fragment thereof. Administration of the further active pharmaceutical agent or chemotherapy may take place immediately, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days or 7 days before and/or after administration of the medicament, composition, antigen-binding protein, or antigen-binding fragment thereof.

In another aspect, there is provided a method for detecting cancer in a subject, the method comprising: contacting a sample obtained from the subject with an antigen-binding protein, or an antigen-binding fragment thereof as disclosed herein in vitro; detecting the binding of the antigen-binding protein, or antigen-binding fragment thereof in the sample; correlating the binding with a level of binding in a control sample to determine the level of binding in the sample, wherein an increase in the level of binding in the sample relative to the control sample is indicative of cancer.

In some embodiments, the control sample is from the same subject. In some embodiments, the control sample is from a different subject.

In some embodiments, in the method disclosed herein, the antigen-binding protein, or antigen-binding fragment thereof may bind to ERBB2 receptor protein kinase. In some embodiments, the antigen-binding protein, or antigen-binding fragment thereof may comprise a detectable label.

As used herein, a detectable label includes fluorescent, chemiluminescent, phosphorescent and chromogenic labels. The label may be constitutively detectable, or may be detectable upon binding with a cell or substrate. Examples of detectable labels include but are not limited to Alexa Fluor® dyes, FITC, TRITC, PE, Texas Red, Cy® dyes, GFP, YFP, RFP, CFP, APC, R-PE, Qdot® probes, SYTOX Green, propidium iodide, biotin, horseradish peroxidase, alkaline phosphatase. In a preferred embodiment, the detectable label is selected from biotin, alkaline phosphatase, horseradish peroxidase, FITC, PE or Cy® Dyes.

The detectable labels may be detected in an assay selected from flow cytometry, tissue section or immunohistochemistry.

In some embodiments, in the method as disclosed herein, the cancer detected may be selected from a cancer that expresses an epitope that the antigen-binding protein, or an antigen-binding fragment thereof as disclosed herein binds.

In preferred embodiments, in the method as disclosed herein, the cancer detected may be selected from breast, colorectal, ovarian, lung, retinoblastoma, gastric, cervical and pancreatic cancer.

In another aspect, there is provided a kit when used in the method as disclosed herein, comprising an antigen-binding protein, or an antigen-binding fragment thereof as disclosed herein, together with instructions for use.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims and non-limiting examples. In addition, where features or aspects of the invention are described in terms of Markush groups, those skilled in the art will recognize that the invention is also thereby described in terms of any individual member or subgroup of members of the Markush group.

EXPERIMENTAL SECTION

Non-limiting examples of the invention and comparative examples will be further described in greater detail by reference to specific Examples, which should not be construed as in any way limiting the scope of the invention.

Materials and Methods

Flow Cytometry Analysis

Cells were harvested using trypsin (Invitrogen, USA) to obtain a single cell suspension of 2×105 cells in 10 μL of ice-cold 1% bovine serum albumin (BSA) (Sigma-Aldrich, USA) in phosphate buffered saline (PBS, Invitrogen, USA). Cells were incubated for 45 minutes at 4° C. in 100 μL of hybridoma culture supernatant containing monoclonal antibody A19 or 5 μg of purified mAbs. Cells were then washed with ice-cold 1% BSA/PBS, and incubated with polyclonal goat anti-mouse immunoglobulin conjugated with fluorescein isothiocyanate (FITC) at a dilution of 1:500 (DAKO, Denmark) for 15 min in the dark. Cells were then washed with ice-cold 1% BSA/PBS and resuspended in 200 μL of 1% BSA/PBS for analysis on FACScalibur flow cytometer (BD Biosciences, USA).

Isotyping

Isotyping was performed with Mouse Monoclonal Antibody Isotyping kit from Roche (Roche, #11493027001). The protocol was carried out according to manufacturer's instructions. Briefly, the pellet in the tube was reconstituted with 150 μl of hybridoma culture supernatant. The solution was thoroughly mixed by vortexing before adding the isostrip. The results were analyzed after 10 min of incubation.

Membrane Protein Extraction

Adherent cells were scraped in PBS (Invitrogen, USA) and centrifuged at 3000 rpm for 5 minutes. The cells were washed in ice-cold PBS (Invitrogen, USA) and centrifuged at 3000 rpm for 5 min. The resulting pellet was resuspended in Homogenize Buffer Mix (BioVision, USA) and sonicated using Misonix Sonicator 3000 under the following conditions: a total process time of 5 min consisting of repeated cycles of 5 s pulse on and 10 seconds pulse off. The resulting homogenate was transferred to a 1.5 mL microcentrifuge tube and centrifuged at 700 g for 10 min at 4° C. to remove debris. The supernatant was then collected and centrifuged at 10000 g for 30 min at 4° C. The resulting supernatant was discarded and the pellet containing membrane protein extract was collected for subsequent analysis.

Immunoprecipitation (IP)

The membrane protein was solubilized with 2% Triton in PBS. Immunoprecipitation was carried out using the Phynexus instrument (Phynexus Inc, California, USA), loaded with Protein G tips (Phynexus Inc, #PTR 92-05-02). The automated program allowed sequential incubation with A19 or Herceptin, solubilized protein samples and washing buffers. Low pH elution was performed at the final step and the eluted sample was neutralized before use.

SDS PAGE Gel and Western Blot

The samples were boiled at 95° C. after adding 5× sample loading dye and subjected to SDS-PAGE using 4-12% gradient NuPAGE Bis-Tris gel (# NP0335 Box) with 1× MOPS buffer (# NP001) (all from Life Technologies). The proteins were separated at 100-120V for 1-2 hr. The samples were prepared in duplicates, one set used for Western blot transfer onto PVDF membrane and the other for silver staining. The membrane blot was blocked with 5% low fat milk for 30 min before incubating overnight at 4° C. with diluted culture supernatant from the primary antibody (1:3) with blocking buffer. Blots were washed with 0.1% Tween in PBS, and incubated with horseradish peroxidase (HRP) conjugated anti-mouse or anti-human Ig (1:10000, DAKO) at room temperature for 1 hr. Finally, the blots were developed using chemiluminescence, ECL prime Western blotting detection reagent (GE Healthcare, # RPN2232). The protein band on the silver stained gel that corresponded to the Western blot was excised and digested with trypsin prior to antigen target identification using mass spectrometry (LC/MS-MS). For target validation, A19 and commercial antibodies against Erbb-2 (Herceptin/Abcam) were diluted 1:100 for IP and 1:1000 for Western blotting.

siRNA Knockdown

To validate the identity of target antigen, knockdown of target antigen was carried out with siRNA against Erbb-2 (Ambion, #103546) using Lipofectamine® RNAiMAX according to the transfection protocol provided by the manufacturer. siRNA negative control was used as the scrambled control. Briefly, 1×105 SKOV3 cells were seeded into 6-well plate and allowed to adhere overnight. Master mixes of Lipofectamine was mixed with master mixes of scrambled and Erbb-2 siRNA (1:1) and allowed to stand for 20 min at room temperature. Culture media was aspirated from the 6-well plate and replaced with 3 ml/well of fresh media. 200 μL of the mix was added into the respective wells dropwise and evenly distributed throughout the wells. The cells were left to incubate at 37° C. for 48 hr. The cells were harvested by scrapping and lysed with 2% Triton in PBS. Total protein concentration was quantified with DC Protein Assay (Bio-Rad Laboratories) and Western blot carried out as previously described.

Periodate

Proteins were resolved by SDS-PAGE and transferred onto PVDF membranes.

The membranes were rinsed twice with 100 mM sodium acetate (Merck, Germany), pH 4.5 and subsequently incubated in the dark twice with 100 mM sodium meta-perlodate (Sigma-Aldrich, USA) for 15 min each. Sodium acetate was added into the control instead of sodium meta-perlodate. After incubation, membranes were rinsed 4 times with 100 mM sodium acetate, followed by PBS. The membranes were then incubated with 0.5M sodium borohydride (Sigma Aldrich, USA) for 30 min at room temperature. After incubation, the membranes were rinsed once with PBS and blocked in 5% milk in PBS-Tween for 30 min at room temperature. Thereafter, the blots were probed with primary antibodies and detection via chemiluminescence.

PNGase Digestion

PNGase digestion was carried out according to manufacturer's protocol (New England Biolabs). Briefly, 10-20 μg of glycoprotein was first denatured in 1× glycoprotein Denaturing Buffer at 95° C. for 10 minutes. Denatured proteins were then incubated with 1 μl sialidase at 37° C. Subsequently, 1× G7 Reaction Buffer and 10% NP-40 were added and incubated with 2 μl of PNGase F at 37° C. for 1 hr. Digested proteins were subsequently resolved on SDS-PAGE and transferred to Western blot.

Inhibition of O-Linked Glycosylation in hESC

Human embryonic stem cell line, HES-3 was obtained from ES Cell International (ESI, Singapore, http://escellinternational). The cells were cultured at 37° C., 5% CO2 on matrigel-coated culture dishes supplemented daily with conditioned media (CM) from immortalized mouse feeders, AE-MEF. The media used for culturing hESC was KNOCK-OUT (KO) media which contained 85% KO-DMEM (DMEM, Dulbecco's modified Eagle's medium) supplemented with 15% KO serum replacer, 1 mM L-glutamine, 25 U/ml penicillin, 25 U/ml streptomycin, 1% non-essential amino acids (NEAA), 0.1 mM 2-mercaptoethanol, and 5 ng/mL of recombinant human fibroblast growth factor-2 (FGF-2) (Invitrogen, Carlsbad, Calif., http://www.invitrogen.com). To passage hESC, briefly, once the culture reached confluency, the cells were mechanically cut with cell cutter (Invitrogen) into small square cell sheets, scraped from the culture dish using cell scraper and transferred to a fresh matrigel-coated culture dish. Culture dishes were pre-incubated with matrigel (Becton Dickinson and Company, Franklin Lakes, N.J., http://www.bd.com) at 4° C. overnight or at room temperature for at least 4 hr. Cells are passaged at a ratio of 1:6 or 1:8 depending on the confluency.

Four days after passaging, hESC in culture were spiked with optimized amount of Benzyl-α-GalNac in CM and incubated for 24 hr. For the negative control, hESC were fed with CM or CM with the same volume of DMSO as the inhibitor. Cells were trypsinsed and resuspended as single cell suspension in 1% BSA/PBS. Flow cytometry analysis was carried out as described previously.

Antibody-Dependent Cell-Mediated Cytotoxicity Assay

ADCC activity was measured using a reporter bioassay (Promega; ADCC Reporter Bioassay, # G7010). The ADCC bioassay was carried out according to the manufacturer's protocol Briefly, cells were seeded at 5,000 cells per well in a 96-well clear bottom black tissue culture plates (Corning; #3904) in low 4% IgG-serum (Promega; # G711A) media. Serial dilutions of primary antibody were incubated in triplicate wells for approximately 15 min at 37° C., 5% CO2. Following incubation, engineered effector cells were added to the wells at approximately 150,000 cells per well. After more than 5 h (or as indicated in results), Bio-Glo™ Luciferase Assay Substrate (Promega; # G719A and # G720A) was added to the wells and luminescence was measured using the Infinite® 200 microplate reader (Tecan).

CellTiter-Glo® (CTG) Luminescent Cell Viability Assay

Cells were seeded (1000 cells/90 μL/well) to 96-well plates (black, clear flat bottom) in culture media and incubated overnight at 37° C., 5% CO2. Stocks of mAbs with varying concentrations or mAb conjugated with toxins were prepared accordingly and added in volumes of 10 μL to the cultures. The cultures were incubated for another 72 hr at 37° C., 5% CO2. Metabolically active cells were measured based on the presence of ATP, using the CellTiter-Glo® (CTG) Luminescent Cell Viability Assay kit (Promega). CTG substrate was added in volumes of 100 μL to each well and incubated for 15 min in the dark at RT on a shaker. Luminescence was measured using TECAN M2000.

Real-Time Monitoring of Cell Proliferation

Cell growth was continuously monitored over time using the xCelligence® real-time analyzer (Roche). Adherence of cells was monitored based on cell impedance. Cell culture media (40 μL) was first loaded onto the 96-well E-plate to measure background impedance. Cells were then plated at 1,000 cells/50 μL per well and allowed to grow overnight in normal cell culture conditions. Stocks of mAbs with varying concentrations or mAb conjugated with toxins were prepared accordingly and spiked in volumes of 10 μL to the cultures. All experiments were done in at least 3 wells per treatment condition.

Antibody Drug Conjugates (ADCs)

Primary mAbs were complexed with appropriate secondary antibody conjugates: mAb-ZAP or HUM-ZAP (Advanced Targeting Systems), at 1:1 molar ratio for 15 min at room temperature before spiking into the cultures. Alternatively, mAbs were biotinylated using the EZ-Link™ Sulfuno-NHS-Biotin kit (Thermo Fisher Scientific) prior to incubating with Streptavidin Saporin (1:1 molar ratio).

Biotinylation of mAbs mAbs were biotinylated using the EZ-Link™ Sulfuno-NHS-Biotin kit (Thermo Fisher Scientific). Briefly, 50 μL of Biotin Regent was added to 1 ml of mAb (2 mg/ml, in PBS) and incubated at room temperature for 30 min. Non-reacted biotin was removed by dialysis.

Internalization Studies

Biotinylated mAbs was incubated with equimolar of pHRodo® Red Avidin (Thermo Fisher Scientific, # P35362) in the dark and on ice for 5 min prior to use. 5 μg of conjugated mAbs was added to the cells and incubated in the dark and at room temperature for 2 hrs before analysis on the FACS Calibur via the FL2-H channel. Real time video capture of the internalization was carried out on the DeltaVision (GE Healthcare Life Sciences).

Immuno-Fluorescence

Cells were trypsinised, seeded at 2000 cells/well on two 24-well plates (Plate 1 and Plate 2) and left overnight in the incubator at 37° C., 5% CO2. Both plates of cells were pre-chilled by washing twice with fresh cold media and topped up with 1 ml of cold media. Primary antibody was then added into the wells (final concentration of 4 μg/ml). For the 1st plate, incubation was carried out on ice for 5 mins. For the 2nd plate, incubation was carried out at 37° C. for an hour to facilitate internalization. After the primary mAb incubation, both plates were washed twice with cold PBS and subsequently fixed with 4% Paraformaldehyde/PBS for 15 min. The cells were washed twice with cold PBS and permeabilized with 0.5% Triton-X/PBS for 10 min. The cells were again washed twice and blocked with 10% Fetal Bovine Serum/PBS for 10 min. The cells were washed twice again with PBS and incubated with anti-mouse Alexafluor® 488 and DAPI (Thermo Fisher Scientific) for 30 min in the dark. Excess dyes were washed off with PBS and 500 μl 1% BSA/PBS was added to each well before imaging.

In Vivo Model

The antibody drug conjugate was prepared by conjugating biotinylated A19 to Streptavidin Saporin (Advanced Targeting Systems) as described earlier. For the animal model, the pre-emptive model was adopted. Each nude mouse was injected in the right flank, subcutaneously, with 5×106 SKOV3 cells in 100 μL volume PBS/matrigel (1:1 volume; BD Matrigel™ Matrix, #354234). The drug (37.5 μg per dose) was administered intra-peritoneal at Day 0, 7 and 14. Tumour size was monitored over 70 days.

Conjugation of mAbs to Fluorophores

Antibodies A19 and Herceptin were conjugated to Alexafluor 488 and Allophycocyanin (APC) respectively using the LYNX Rapid Conjugation Kit® (AbD Serotec) according to manufacturer's protocol. Briefly, 100-150 μg of antibody is used for every 100 μg of fluorophore. To the antibody sample, 1 μl of the Modifier reagent is added to every 10 μl of antibody and gently mixed. The mixed antibody-modifier sample is added directly onto the LYNX lyophilized is resuspended by gentle pipetting the solution up and down twice. The sample is incubated at room temperature for 3 hr. After the incubation, 1 μl of Quencher is added to every 10 μl antibody used. The final sample is left to stand for 30 min before use.

Competitive Assay

5 μg of conjugated mAbs were incubated individually or dually with single cells suspension of SKOV3 (0.5×106 cells per 100 μl 1% BSA/PBS) on ice for 30 min. The cells were washed and resuspended in 200 μl buffer. Bindings of A19 and Herceptin were analysed on the FACS Calibur via the FL1-H and FL4-H channels respectively.

Results

The experimental data demonstrates that A19 binds to various cancer cell lines and that the isotype of A19 is IgG1. From immunoprecipitation/mass spectrometry, the antigen target of A19 is shown to be Erbb-2. A19 binds to two isoforms. The upper band in FIG. 3 is identified as Isoform 4 of Receptor Tyrosine Kinase while the lower band is identified as Receptor tyrosine-protein kinase Erbb2. The peptide coverage (from MS) compared to the protein sequence for A19 is: (1) 39% for Isoform 4 of Receptor Tyrosine Kinase. (2) 14% for Receptor tyrosine-protein kinase Erbb-2.

Immunoprecipitation (IP) was carried out with A19 and immunoblotted with Herceptin. Similarly, IP was carried out with Herceptin and immunoblotted with A19. In both experiments, the same antigen was detected confirming that the antigen target of A19 is Erbb-2.

Knock down of Erbb-2 was carried out using siRNA. Protein load across all conditions (LP, SC and KD) were normalized as evident by the actin bands. Binding of anti-Erbb-2 and Herceptin was diminished in the KD lane but not in the other 2 controls, confirming the knock down of Erbb-2. Diminished binding of A19 was also observed, confirming that the antigen target of A19 is indeed Erbb-2.

For the perlodate assay, sodium metaperiodate was used to oxidize the carbohydrate moiety of the glycoproteins by opening saccharide rings of vicinal diols, producing 2 aldehyde groups which are reduced to hydroxyls by the reducing agent sodium borohydride. Upon treatment with perlodate, the binding of Herceptin and A19 was abolished. This shows that A19 is binding to glycans on Erbb-2.

Upon enzymatic removal of N-linked glycans by PNGase, the binding of Herceptin and A19 was abolished. This shows that A19 binds to N-linked glycans on Erbb-2.

O-linked glycan synthesis was inhibited in culture with Benzyl-alpha-GalNAc. The loss of O-linked glycans was confirmed by the loss of binding of TRA-1-60 post-inhibition. The binding of Herceptin and A19 to Benzyl-alpha-GalNAc treated cells was similar to the controls, confirming that the binding of A19 is not to O-linked glycans.

The variable genes from A19 mouse hybridoma were isolated and cloned into multi-promoter single expression vectors containing human $IgG_1$ constant genes. These vectors were then transfected into DG44 Chinese hamster ovary (CHO) mammalian cell lines for production. The chimeric A19 was tested for ADCC activity using an ADCC reporter bio-assay (Promega). Herceptin exhibited ADCC activity when cultured with either ovarian and breast cancer cells. However, A19 does not exhibit ADCC activity when cultured with either ovarian and breast cancer cells. As a naked antibody, A19 has no effect on the proliferation of SKOV3 and has no effect on the proliferation of SKOV3.

When the cells were incubated with pHRodo dye (negative control), there was no shift in fluorescence. When the cells were incubated with the positive control mAb 2448 (conjugated to pHRodo), an increase in fluorescence was observed. Similarly, cells incubated with A19 conjugated with pHRodo showed an increase in fluorescence, indicating that the mAb internalizes into the cells.

The immunofluorescence staining confirms that A19 internalizes into cells. Viabilities of the cells were comparable when incubated with A19 or saporin-toxin alone. As an ADC, A19 kills cells in vitro and kills cells that highly express Erbb-2.

Based on the binding of A19 and through flow cytometry analysis, SKOV3 and SKBR3 express high levels of Erbb-2. The other 4 cell lines express moderate or low levels of Erbb-2 (compared to SKOV3 and SKBR3). The viabilities of COLO205, MCF-7, CAMA-1 and BT474 remained high when incubated with A19-ADC. On the other hand, the viabilities of SKOV3 and SKBR3 were significantly reduced when incubated with A19-ADC, indicating that as an ADC, A19 kills cells that highly express Erbb-2.

Through real-time monitoring, A19-ADC kills cells in a dosage dependent manner. It is noted that the dosage used is 1000× lower compared to that of naked A19.

A19-ADC was generated via biotinylation of the mAb and conjugated to streptavidin-Saporin. Although this conjugation was sub-optimal, the A19-ADC is able to suppress tumour growth in vivo. On the contrary, in the other 2 control groups (Saporin or A19 only), tumour suppression was not observed.

When A19 and Herceptin were incubated together with the cells, they do not compete with each other. This shows that A19 and Herceptin bind to different epitopes. All 3 mAbs (A19, Herceptin and commercial antibody) detect various sets of Erbb-2 isoforms. The isoform that is probably common to the 3 mAbs is the upper band or isoform 4.

What is claimed is:

1. An antigen-binding protein, or an antigen-binding fragment thereof, comprising (i) a heavy chain variable domain comprising a VHCDR1 having the amino acid sequence GYTFSNYWIE (SEQ ID NO: 3); a VHCDR2 having the amino acid sequence EILPGSDSTNYNEKFKG (SEQ ID NO: 4), and a VHCDR3 having the amino acid sequence GGSNYGYYFDY (SEQ ID NO: 5); and (ii) a light chain variable domain comprising a VLCDR1 having the amino acid sequence KASQDVGTAVA (SEQ ID NO: 6), a VLCDR2 having the amino acid sequence WASTRHT (SEQ ID NO: 7), and a VLCDR3 having the amino acid sequence QQYSSYRT (SEQ ID NO: 8).

2. The antigen-binding protein, or antigen-binding fragment thereof, as claimed in claim 1, wherein the heavy chain variable region comprises the amino acid sequence set forth in SEQ ID NO:1.

3. The antigen-binding protein, or antigen-binding fragment thereof, as claimed in claim 1, wherein the light chain variable region comprises the amino acid sequence set forth in SEQ ID NO:2.

4. The antigen-binding protein, or antigen-binding fragment thereof, as claimed in claim 1, optionally wherein the antigen binding protein is a monoclonal antibody; optionally wherein the monoclonal antibody is humanized.

5. The antigen-binding protein, or antigen-binding fragment thereof, as claimed in claim 1, wherein the antigen-binding protein, or antigen-binding fragment thereof, binds to ERBB2 receptor protein kinase; optionally wherein the antigen-binding protein, or an antigen-binding fragment thereof binds to isoform 4 of ERBB2 receptor protein kinase; optionally wherein the antigen-binding protein, or antigen-binding fragment thereof binds to a truncated isoform 4 of ERBB2 receptor protein kinase; optionally wherein the truncated isoform 4 does not comprise any hydrophobic regions; optionally wherein the antigen-binding protein, or antigen-binding fragment thereof binds to a glycan on the ERBB2 receptor protein kinase; optionally wherein the antigen-binding protein, or antigen-binding fragment thereof binds to an N-linked glycan on the ERBB2 receptor protein kinase; optionally wherein the antigen-binding protein, or antigen-binding fragment thereof binds to an N-linked glycan located at one or more of amino acid positions 66, 124, 187, 259, 530, 571 and 629 of ERBB2 receptor protein kinase.

6. An antigen-binding protein or an antigen-binding fragment thereof, that competes with the antigen binding protein as claimed in claim 1 for binding to ERBB2 receptor protein kinase.

7. The antigen-binding protein, or an antigen-binding fragment thereof, as claimed in claim 1, comprising a radioisotope or a cytotoxin conjugated thereto.

8. The antigen-binding protein, or antigen-binding fragment thereof, as claimed in claim 7, wherein the antibody is conjugated with a cytotoxin selected from the group consisting of monomethyl auristatin E (MMEA-1), mertansine (DM-1) and saporin; optionally wherein the antigen-binding protein, or an antigen-binding fragment comprising a radioisotope or cytotoxin conjugated thereto is internalized into a cell upon binding to ERBB2 receptor tyrosine kinase.

9. The antigen-binding protein, or antigen-binding fragment thereof as claimed in claim 1, wherein the antigen-binding protein, or antigen-binding fragment thereof is formulated as a composition comprising a physiologically acceptable carrier.

10. The antigen-binding protein, or antigen-binding fragment thereof as claimed in claim 9, wherein the composition comprises a further active pharmaceutical ingredient selected from, carboplatin.

11. A method of treating cancer comprising administering an antigen-binding protein, or an antigen-binding fragment thereof, to a subject in need thereof, wherein the antigen-binding protein, or an antigen-binding fragment thereof, comprises (i) a heavy chain variable domain comprising a VHCDR1 having the amino acid sequence GYTFSNYWIE (SEQ ID NO: 3); a VHCDR2 having the amino acid sequence EILPGSDSTNYNEKFKG (SEQ ID NO: 4), and a VHCDR3 having the amino acid sequence GGSNYGYYFDY (SEQ ID NO: 5); (ii) a light chain variable domain comprising a VLCDR1 having the amino acid sequence KASQDVGTAVA (SEQ ID NO: 6), a VLCDR2 having the amino acid sequence WASTRHT (SEQ ID NO: 7), and a VLCDR3 having the amino acid sequence QQYSSYRT (SEQ ID NO: 8), and the antigen-binding protein, or antigen-binding fragment thereof, further comprising a radioisotope or a cytotoxin conjugated thereto.

12. The method of claim 11, wherein the cancer is selected from breast cancer; optionally wherein the method comprises administering a further active pharmaceutical ingredient to the subject; optionally wherein the antigen-binding protein, or an antigen-binding fragment thereof is administered with chemotherapy; optionally wherein the further pharmaceutical agent or chemotherapy is administered separately, simultaneously or sequentially.

* * * * *

SEQUENCE LISTING

```
<160> NUMBER OF SEQ ID NOS: 12

<210> SEQ ID NO 1
<211> LENGTH: 120
<212> TYPE: PRT
<213> ORGANISM: Artificial Sequence
<220> FEATURE:
<223> OTHER INFORMATION: Isolated peptide sequence

<400> SEQUENCE: 1

Gln Val Lys Leu Gln Glu Ser Gly Ala Glu Leu Met Lys Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
```

```
        35                  40                  45

Gly Glu Ile Leu Pro Gly Ser Asp Ser Thr Asn Tyr Asn Glu Lys Phe
    50                  55                  60

Lys Gly Lys Ala Thr Phe Thr Ala Asp Thr Ser Ser Asn Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Ser Asn Tyr Gly Tyr Tyr Phe Asp Tyr Trp Gly Gln
            100                 105                 110

Gly Thr Thr Val Thr Val Ser Ser
        115                 120


<210> SEQ ID NO 2
<211> LENGTH: 107
<212> TYPE: PRT
<213> ORGANISM: Artificial Sequence
<220> FEATURE:
<223> OTHER INFORMATION: Isolated peptide sequence

<400> SEQUENCE: 2

Asp Ile Leu Met Thr Gln Ser His Lys Phe Met Ser Thr Ser Val Gly
1               5                   10                  15

Asp Arg Val Ser Ile Pro Cys Lys Ala Ser Gln Asp Val Gly Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg His Thr Gly Val Pro Asp Arg Phe Thr Gly
    50                  55                  60

Ser Gly Ser Gly Thr Asp Phe Thr Leu Ser Ile Ser Asn Val Gln Ser
65                  70                  75                  80

Glu Asp Leu Ala Asp Tyr Phe Cys Gln Gln Tyr Ser Ser Tyr Arg Thr
                85                  90                  95

Phe Gly Gly Gly Thr Lys Leu Glu Ile Lys Arg
            100                 105


<210> SEQ ID NO 3
<211> LENGTH: 10
<212> TYPE: PRT
<213> ORGANISM: Artificial Sequence
<220> FEATURE:
<223> OTHER INFORMATION: Isolated peptide sequence

<400> SEQUENCE: 3

Gly Tyr Thr Phe Ser Asn Tyr Trp Ile Glu
1               5                   10


<210> SEQ ID NO 4
<211> LENGTH: 17
<212> TYPE: PRT
<213> ORGANISM: Artificial Sequence
<220> FEATURE:
<223> OTHER INFORMATION: Isolated peptide sequence

<400> SEQUENCE: 4

Glu Ile Leu Pro Gly Ser Asp Ser Thr Asn Tyr Asn Glu Lys Phe Lys
1               5                   10                  15

Gly


<210> SEQ ID NO 5
<211> LENGTH: 11
```

<212> TYPE: PRT
<213> ORGANISM: Artificial Sequence
<220> FEATURE:
<223> OTHER INFORMATION: Isolated peptide sequence

<400> SEQUENCE: 5

Gly Gly Ser Asn Tyr Gly Tyr Tyr Phe Asp Tyr
1 5 10

<210> SEQ ID NO 6
<211> LENGTH: 11
<212> TYPE: PRT
<213> ORGANISM: Artificial Sequence
<220> FEATURE:
<223> OTHER INFORMATION: Isolated peptide sequence

<400> SEQUENCE: 6

Lys Ala Ser Gln Asp Val Gly Thr Ala Val Ala
1 5 10

<210> SEQ ID NO 7
<211> LENGTH: 7
<212> TYPE: PRT
<213> ORGANISM: Artificial Sequence
<220> FEATURE:
<223> OTHER INFORMATION: Isolated peptide sequence

<400> SEQUENCE: 7

Trp Ala Ser Thr Arg His Thr
1 5

<210> SEQ ID NO 8
<211> LENGTH: 8
<212> TYPE: PRT
<213> ORGANISM: Artificial Sequence
<220> FEATURE:
<223> OTHER INFORMATION: Isolated peptide sequence

<400> SEQUENCE: 8

Gln Gln Tyr Ser Ser Tyr Arg Thr
1 5

<210> SEQ ID NO 9
<211> LENGTH: 360
<212> TYPE: DNA
<213> ORGANISM: Artificial Sequence
<220> FEATURE:
<223> OTHER INFORMATION: Isolated nucleotide sequence

<400> SEQUENCE: 9
caggtgaagc tgcaggagtc tggagctgag ctgatgaagc ctggggcctc agtgaagata 60
tcctgcaagg ctactggcta cacattcagt aactactgga tagagtgggt aaagcagagg 120
cctggacatg gccttgagtg gattggagag attttacctg gaagtgatag tactaactac 180
aatgagaagt tcaagggcaa ggccacattc actgcagata catcctccaa cacagcctac 240
atgcaactca gcagcctgac atctgaggac tctgccgtct attactgtgc aagaggaggg 300
tcgaactacg ggtactactt tgactactgg ggccaaggga ccacggtcac cgtctcctca 360

<210> SEQ ID NO 10
<211> LENGTH: 321
<212> TYPE: DNA
<213> ORGANISM: Artificial Sequence
<220> FEATURE:
<223> OTHER INFORMATION: Isolated nucleotide sequence

<400> SEQUENCE: 10

```
gacattctga tgacccagtc tcacaaattc atgtccacat cagtaggaga cagggtcagc     60
atcccctgca aggccagtca ggatgtgggt actgctgtag cctggtatca acaaaaacca    120
gggcaatctc ctaaactact gatttactgg gcatccaccc ggcacactgg agtccctgat    180
cgcttcacag gcagtggatc tgggacagat ttcactctct ccattagcaa tgtgcagtct    240
gaagacttgg cagattattt ctgtcagcaa tatagcagct atcggacgtt cggtggaggc    300
accaagctgg aaatcaaacg g                                              321
```

<210> SEQ ID NO 11
<211> LENGTH: 1240
<212> TYPE: PRT
<213> ORGANISM: Artificial Sequence
<220> FEATURE:
<223> OTHER INFORMATION: Isolated peptide sequence

<400> SEQUENCE: 11

```
Met Pro Arg Gly Ser Trp Lys Pro Gln Val Cys Thr Gly Thr Asp Met
1               5                   10                  15

Lys Leu Arg Leu Pro Ala Ser Pro Glu Thr His Leu Asp Met Leu Arg
            20                  25                  30

His Leu Tyr Gln Gly Cys Gln Val Val Gln Gly Asn Leu Glu Leu Thr
        35                  40                  45

Tyr Leu Pro Thr Asn Ala Ser Leu Ser Phe Leu Gln Asp Ile Gln Glu
    50                  55                  60

Val Gln Gly Tyr Val Leu Ile Ala His Asn Gln Val Arg Gln Val Pro
65                  70                  75                  80

Leu Gln Arg Leu Arg Ile Val Arg Gly Thr Gln Leu Phe Glu Asp Asn
                85                  90                  95

Tyr Ala Leu Ala Val Leu Asp Asn Gly Asp Pro Leu Asn Asn Thr Thr
            100                 105                 110

Pro Val Thr Gly Ala Ser Pro Gly Gly Leu Arg Glu Leu Gln Leu Arg
        115                 120                 125

Ser Leu Thr Glu Ile Leu Lys Gly Gly Val Leu Ile Gln Arg Asn Pro
    130                 135                 140

Gln Leu Cys Tyr Gln Asp Thr Ile Leu Trp Lys Asp Ile Phe His Lys
145                 150                 155                 160

Asn Asn Gln Leu Ala Leu Thr Leu Ile Asp Thr Asn Arg Ser Arg Ala
                165                 170                 175

Cys His Pro Cys Ser Pro Met Cys Lys Gly Ser Arg Cys Trp Gly Glu
            180                 185                 190

Ser Ser Glu Asp Cys Gln Ser Leu Thr Arg Thr Val Cys Ala Gly Gly
        195                 200                 205

Cys Ala Arg Cys Lys Gly Pro Leu Pro Thr Asp Cys Cys His Glu Gln
    210                 215                 220

Cys Ala Ala Gly Cys Thr Gly Pro Lys His Ser Asp Cys Leu Ala Cys
225                 230                 235                 240

Leu His Phe Asn His Ser Gly Ile Cys Glu Leu His Cys Pro Ala Leu
                245                 250                 255

Val Thr Tyr Asn Thr Asp Thr Phe Glu Ser Met Pro Asn Pro Glu Gly
            260                 265                 270

Arg Tyr Thr Phe Gly Ala Ser Cys Val Thr Ala Cys Pro Tyr Asn Tyr
        275                 280                 285

Leu Ser Thr Asp Val Gly Ser Cys Thr Leu Val Cys Pro Leu His Asn
```

-continued

```
    290                 295                 300

Gln Glu Val Thr Ala Glu Asp Gly Thr Gln Arg Cys Glu Lys Cys Ser
305                 310                 315                 320

Lys Pro Cys Ala Arg Val Cys Tyr Gly Leu Gly Met Glu His Leu Arg
                325                 330                 335

Glu Val Arg Ala Val Thr Ser Ala Asn Ile Gln Glu Phe Ala Gly Cys
            340                 345                 350

Lys Lys Ile Phe Gly Ser Leu Ala Phe Leu Pro Glu Ser Phe Asp Gly
        355                 360                 365

Asp Pro Ala Ser Asn Thr Ala Pro Leu Gln Pro Glu Gln Leu Gln Val
    370                 375                 380

Phe Glu Thr Leu Glu Glu Ile Thr Gly Tyr Leu Tyr Ile Ser Ala Trp
385                 390                 395                 400

Pro Asp Ser Leu Pro Asp Leu Ser Val Phe Gln Asn Leu Gln Val Ile
                405                 410                 415

Arg Gly Arg Ile Leu His Asn Gly Ala Tyr Ser Leu Thr Leu Gln Gly
            420                 425                 430

Leu Gly Ile Ser Trp Leu Gly Leu Arg Ser Leu Arg Glu Leu Gly Ser
        435                 440                 445

Gly Leu Ala Leu Ile His His Asn Thr His Leu Cys Phe Val His Thr
    450                 455                 460

Val Pro Trp Asp Gln Leu Phe Arg Asn Pro His Gln Ala Leu Leu His
465                 470                 475                 480

Thr Ala Asn Arg Pro Glu Asp Glu Cys Val Gly Glu Gly Leu Ala Cys
                485                 490                 495

His Gln Leu Cys Ala Arg Gly His Cys Trp Gly Pro Gly Pro Thr Gln
            500                 505                 510

Cys Val Asn Cys Ser Gln Phe Leu Arg Gly Gln Glu Cys Val Glu Glu
        515                 520                 525

Cys Arg Val Leu Gln Gly Leu Pro Arg Glu Tyr Val Asn Ala Arg His
    530                 535                 540

Cys Leu Pro Cys His Pro Glu Cys Gln Pro Gln Asn Gly Ser Val Thr
545                 550                 555                 560

Cys Phe Gly Pro Glu Ala Asp Gln Cys Val Ala Cys Ala His Tyr Lys
                565                 570                 575

Asp Pro Pro Phe Cys Val Ala Arg Cys Pro Ser Gly Val Lys Pro Asp
            580                 585                 590

Leu Ser Tyr Met Pro Ile Trp Lys Phe Pro Asp Glu Glu Gly Ala Cys
        595                 600                 605

Gln Pro Cys Pro Ile Asn Cys Thr His Ser Cys Val Asp Leu Asp Asp
    610                 615                 620

Lys Gly Cys Pro Ala Glu Gln Arg Ala Ser Pro Leu Thr Ser Ile Ile
625                 630                 635                 640

Ser Ala Val Val Gly Ile Leu Leu Val Val Val Leu Gly Val Val Phe
                645                 650                 655

Gly Ile Leu Ile Lys Arg Arg Gln Gln Lys Ile Arg Lys Tyr Thr Met
            660                 665                 670

Arg Arg Leu Leu Gln Glu Thr Glu Leu Val Glu Pro Leu Thr Pro Ser
        675                 680                 685

Gly Ala Met Pro Asn Gln Ala Gln Met Arg Ile Leu Lys Glu Thr Glu
    690                 695                 700

Leu Arg Lys Val Lys Val Leu Gly Ser Gly Ala Phe Gly Thr Val Tyr
705                 710                 715                 720
```

```
Lys Gly Ile Trp Ile Pro Asp Gly Glu Asn Val Lys Ile Pro Val Ala
                725                 730                 735

Ile Lys Val Leu Arg Glu Asn Thr Ser Pro Lys Ala Asn Lys Glu Ile
            740                 745                 750

Leu Asp Glu Ala Tyr Val Met Ala Gly Val Gly Ser Pro Tyr Val Ser
        755                 760                 765

Arg Leu Leu Gly Ile Cys Leu Thr Ser Thr Val Gln Leu Val Thr Gln
    770                 775                 780

Leu Met Pro Tyr Gly Cys Leu Leu Asp His Val Arg Glu Asn Arg Gly
785                 790                 795                 800

Arg Leu Gly Ser Gln Asp Leu Leu Asn Trp Cys Met Gln Ile Ala Lys
                805                 810                 815

Gly Met Ser Tyr Leu Glu Asp Val Arg Leu Val His Arg Asp Leu Ala
            820                 825                 830

Ala Arg Asn Val Leu Val Lys Ser Pro Asn His Val Lys Ile Thr Asp
        835                 840                 845

Phe Gly Leu Ala Arg Leu Leu Asp Ile Asp Glu Thr Glu Tyr His Ala
    850                 855                 860

Asp Gly Gly Lys Val Pro Ile Lys Trp Met Ala Leu Glu Ser Ile Leu
865                 870                 875                 880

Arg Arg Arg Phe Thr His Gln Ser Asp Val Trp Ser Tyr Gly Val Thr
                885                 890                 895

Val Trp Glu Leu Met Thr Phe Gly Ala Lys Pro Tyr Asp Gly Ile Pro
            900                 905                 910

Ala Arg Glu Ile Pro Asp Leu Leu Glu Lys Gly Glu Arg Leu Pro Gln
        915                 920                 925

Pro Pro Ile Cys Thr Ile Asp Val Tyr Met Ile Met Val Lys Cys Trp
    930                 935                 940

Met Ile Asp Ser Glu Cys Arg Pro Arg Phe Arg Glu Leu Val Ser Glu
945                 950                 955                 960

Phe Ser Arg Met Ala Arg Asp Pro Gln Arg Phe Val Val Ile Gln Asn
                965                 970                 975

Glu Asp Leu Gly Pro Ala Ser Pro Leu Asp Ser Thr Phe Tyr Arg Ser
            980                 985                 990

Leu Leu Glu Asp Asp Asp Met Gly  Asp Leu Val Asp Ala  Glu Glu Tyr
        995                 1000                1005

Leu Val  Pro Gln Gln Gly Phe  Phe Cys Pro Asp Pro  Ala Pro Gly
    1010                1015                1020

Ala Gly  Gly Met Val His His  Arg His Arg Ser Ser  Ser Thr Arg
    1025                1030                1035

Ser Gly  Gly Gly Asp Leu Thr  Leu Gly Leu Glu Pro  Ser Glu Glu
    1040                1045                1050

Glu Ala  Pro Arg Ser Pro Leu  Ala Pro Ser Glu Gly  Ala Gly Ser
    1055                1060                1065

Asp Val  Phe Asp Gly Asp Leu  Gly Met Gly Ala Ala  Lys Gly Leu
    1070                1075                1080

Gln Ser  Leu Pro Thr His Asp  Pro Ser Pro Leu Gln  Arg Tyr Ser
    1085                1090                1095

Glu Asp  Pro Thr Val Pro Leu  Pro Ser Glu Thr Asp  Gly Tyr Val
    1100                1105                1110

Ala Pro  Leu Thr Cys Ser Pro  Gln Pro Glu Tyr Val  Asn Gln Pro
    1115                1120                1125
```

```
Asp Val  Arg Pro Gln Pro Pro  Ser Pro Arg Glu Gly  Pro Leu Pro
    1130                 1135                 1140

Ala Ala  Arg Pro Ala Gly Ala  Thr Leu Glu Arg Pro  Lys Thr Leu
    1145                 1150                 1155

Ser Pro  Gly Lys Asn Gly Val  Val Lys Asp Val Phe  Ala Phe Gly
    1160                 1165                 1170

Gly Ala  Val Glu Asn Pro Glu  Tyr Leu Thr Pro Gln  Gly Gly Ala
    1175                 1180                 1185

Ala Pro  Gln Pro His Pro Pro  Pro Ala Phe Ser Pro  Ala Phe Asp
    1190                 1195                 1200

Asn Leu  Tyr Tyr Trp Asp Gln  Asp Pro Pro Glu Arg  Gly Ala Pro
    1205                 1210                 1215

Pro Ser  Thr Phe Lys Gly Thr  Pro Thr Ala Glu Asn  Pro Glu Tyr
    1220                 1225                 1230

Leu Gly  Leu Asp Val Pro Val
    1235                 1240


<210> SEQ ID NO 12
<211> LENGTH: 603
<212> TYPE: PRT
<213> ORGANISM: Artificial Sequence
<220> FEATURE:
<223> OTHER INFORMATION: Isolated peptide sequence

<400> SEQUENCE: 12

Met Lys Leu Arg Leu Pro Ala Ser Pro Glu Thr His Leu Asp Met Leu
1               5                   10                  15

Arg His Leu Tyr Gln Gly Cys Gln Val Val Gln Gly Asn Leu Glu Leu
            20                  25                  30

Thr Tyr Leu Pro Thr Asn Ala Ser Leu Ser Phe Leu Gln Asp Ile Gln
        35                  40                  45

Glu Val Gln Gly Tyr Val Leu Ile Ala His Asn Gln Val Arg Gln Val
    50                  55                  60

Pro Leu Gln Arg Leu Arg Ile Val Arg Gly Thr Gln Leu Phe Glu Asp
65                  70                  75                  80

Asn Tyr Ala Leu Ala Val Leu Asp Asn Gly Asp Pro Leu Asn Asn Thr
                85                  90                  95

Thr Pro Val Thr Gly Ala Ser Pro Gly Gly Leu Arg Glu Leu Gln Leu
            100                 105                 110

Arg Ser Leu Thr Glu Ile Leu Lys Gly Gly Val Leu Ile Gln Arg Asn
        115                 120                 125

Pro Gln Leu Cys Tyr Gln Asp Thr Ile Leu Trp Lys Asp Ile Phe His
    130                 135                 140

Lys Asn Asn Gln Leu Ala Leu Thr Leu Ile Asp Thr Asn Arg Ser Arg
145                 150                 155                 160

Ala Cys His Pro Cys Ser Pro Met Cys Lys Gly Ser Arg Cys Trp Gly
                165                 170                 175

Glu Ser Ser Glu Asp Cys Gln Ser Leu Thr Arg Thr Val Cys Ala Gly
            180                 185                 190

Gly Cys Ala Arg Cys Lys Gly Pro Leu Pro Thr Asp Cys Cys His Glu
        195                 200                 205

Gln Cys Ala Ala Gly Cys Thr Gly Pro Lys His Ser Asp Cys Leu Ala
    210                 215                 220

Cys Leu His Phe Asn His Ser Gly Ile Cys Glu Leu His Cys Pro Ala
225                 230                 235                 240
```

-continued

```
Leu Val Thr Tyr Asn Thr Asp Thr Phe Glu Ser Met Pro Asn Pro Glu
                245                 250                 255

Gly Arg Tyr Thr Phe Gly Ala Ser Cys Val Thr Ala Cys Pro Tyr Asn
            260                 265                 270

Tyr Leu Ser Thr Asp Val Gly Ser Cys Thr Leu Val Cys Pro Leu His
        275                 280                 285

Asn Gln Glu Val Thr Ala Glu Asp Gly Thr Gln Arg Cys Glu Lys Cys
    290                 295                 300

Ser Lys Pro Cys Ala Arg Val Cys Tyr Gly Leu Gly Met Glu His Leu
305                 310                 315                 320

Arg Glu Val Arg Ala Val Thr Ser Ala Asn Ile Gln Glu Phe Ala Gly
                325                 330                 335

Cys Lys Lys Ile Phe Gly Ser Leu Ala Phe Leu Pro Glu Ser Phe Asp
            340                 345                 350

Gly Asp Pro Ala Ser Asn Thr Ala Pro Leu Gln Pro Glu Gln Leu Gln
        355                 360                 365

Val Phe Glu Thr Leu Glu Glu Ile Thr Gly Tyr Leu Tyr Ile Ser Ala
    370                 375                 380

Trp Pro Asp Ser Leu Pro Asp Leu Ser Val Phe Gln Asn Leu Gln Val
385                 390                 395                 400

Ile Arg Gly Arg Ile Leu His Asn Gly Ala Tyr Ser Leu Thr Leu Gln
                405                 410                 415

Gly Leu Gly Ile Ser Trp Leu Gly Leu Arg Ser Leu Arg Glu Leu Gly
            420                 425                 430

Ser Gly Leu Ala Leu Ile His His Asn Thr His Leu Cys Phe Val His
        435                 440                 445

Thr Val Pro Trp Asp Gln Leu Phe Arg Asn Pro His Gln Ala Leu Leu
    450                 455                 460

His Thr Ala Asn Arg Pro Glu Asp Glu Cys Val Gly Glu Gly Leu Ala
465                 470                 475                 480

Cys His Gln Leu Cys Ala Arg Gly His Cys Trp Gly Pro Gly Pro Thr
                485                 490                 495

Gln Cys Val Asn Cys Ser Gln Phe Leu Arg Gly Gln Glu Cys Val Glu
            500                 505                 510

Glu Cys Arg Val Leu Gln Gly Leu Pro Arg Glu Tyr Val Asn Ala Arg
        515                 520                 525

His Cys Leu Pro Cys His Pro Glu Cys Gln Pro Gln Asn Gly Ser Val
    530                 535                 540

Thr Cys Phe Gly Pro Glu Ala Asp Gln Cys Val Ala Cys Ala His Tyr
545                 550                 555                 560

Lys Asp Pro Pro Phe Cys Val Ala Arg Cys Pro Ser Gly Val Lys Pro
                565                 570                 575

Asp Leu Ser Tyr Met Pro Ile Trp Lys Phe Pro Asp Glu Glu Gly Ala
            580                 585                 590

Cys Gln Pro Cys Pro Ile Asn Cys Thr His Ser
        595                 600
```